(12) United States Patent
Tilk et al.

(10) Patent No.: US 9,655,561 B2
(45) Date of Patent: May 23, 2017

(54) MULTI-LAYERED SENSOR APPARATUS

(75) Inventors: Jason Tilk, Cleveland Heights, OH (US); Jeffrey S. Taggart, Cleveland Heights, OH (US); Lindsey Tufts, Jr., Eastlake, OH (US); David L. Bacon, Keene, NH (US); Paul Durant, Jr., Andover, MA (US); Harold Wodlinger, Thornhill (CA); Charulatha Ramanathan, Solon, OH (US); Steven G. Arless, Baie Durfe (CA)

(73) Assignee: Cardioinsight Technologies, Inc., Cleveland, OH (US)

( * ) Notice: Subject to any disclaimer, the term of this patent is extended or adjusted under 35 U.S.C. 154(b) by 837 days.

(21) Appl. No.: 13/995,807

(22) PCT Filed: Dec. 22, 2011

(86) PCT No.: PCT/US2011/066796
§ 371 (c)(1),
(2), (4) Date: Jun. 19, 2013

(87) PCT Pub. No.: WO2012/088398
PCT Pub. Date: Jun. 28, 2012

(65) Prior Publication Data
US 2013/0281814 A1 Oct. 24, 2013

Related U.S. Application Data

(60) Provisional application No. 61/426,143, filed on Dec. 22, 2010.

(51) Int. Cl.
*A61B 5/04* (2006.01)
*A61B 5/00* (2006.01)
*A61B 5/0408* (2006.01)

(52) U.S. Cl.
CPC ........ *A61B 5/6823* (2013.01); *A61B 5/04085* (2013.01); *A61B 5/6805* (2013.01); *A61B 2560/0468* (2013.01); *A61B 2562/046* (2013.01)

(58) Field of Classification Search
CPC .. A61N 1/0484; A61N 1/3925; A61B 5/0006; A61B 5/04012; A61B 5/6804;
(Continued)

(56) References Cited

U.S. PATENT DOCUMENTS

| 4,583,547 A | 4/1986 | Granek et al. |
| 4,608,987 A | 9/1986 | Mills |

(Continued)

FOREIGN PATENT DOCUMENTS

| EP | 0 458 883 B1 | 11/1996 |
| EP | 0 571 040 B1 | 10/1997 |

(Continued)

OTHER PUBLICATIONS

Extended European Search Report for corresponding EP11851242.5 dated Aug. 17, 2015; Completed by J Sopelana Martinez of Munich on Aug. 7, 2015.

(Continued)

*Primary Examiner* — Joseph Stoklosa
*Assistant Examiner* — Brian M Antiskay
(74) *Attorney, Agent, or Firm* — Tarolli, Sundheim, Covell & Tummino LLP

(57) ABSTRACT

A sensor array system (10, 30) can include a substrate layer (12, 14) that includes a stretchable and conformable material that is configured to allow spaced apart and interconnected portions thereof to stretch and conform commensurate with movement of the substrate layer (12, 14), such as when attached to a patient's body. A plurality of electrodes (16) are disposed on a contact surface of the substrate layer (12, 14).

(Continued)

Electrically conductive paths are also disposed on the substrate layer (14) and extending from each of the electrodes to which it is connected and terminating in an end thereof. The substrate layer may itself include more than one layer, such as including a flexible substrate layer (12) that is affixed to a stretchable material layer (14).

33 Claims, 11 Drawing Sheets

(58) Field of Classification Search
CPC . A61B 5/0476; A61B 5/6805; A61B 5/02438;
A61B 5/0245; A61B 5/0402; A61B
5/0488
USPC ........ 600/300, 372, 382, 384–393, 508–509;
607/2–9, 115–119
See application file for complete search history.

(56) References Cited

U.S. PATENT DOCUMENTS

| | | | |
|---|---|---|---|
| 4,852,572 A | 8/1989 | Nakahashi et al. | |
| 4,957,109 A | 9/1990 | Groeger et al. | |
| 4,987,901 A | 1/1991 | Kunig | |
| 5,025,808 A | 6/1991 | Hafner | |
| 5,042,481 A | 8/1991 | Suzuki et al. | |
| 5,184,620 A | 2/1993 | Cudahy et al. | |
| 5,257,631 A | 11/1993 | Wilk | |
| 5,339,820 A | 8/1994 | Henry et al. | |
| 5,353,793 A | 10/1994 | Bornn | |
| 5,483,967 A | 1/1996 | Ohtake | |
| 5,511,553 A | 4/1996 | Segalowitz | |
| 5,865,740 A | 2/1999 | Kelly et al. | |
| 5,868,671 A | 2/1999 | Mahoney | |
| 5,995,861 A | 11/1999 | Price | |
| 6,033,370 A | 3/2000 | Reinbold et al. | |
| 6,047,203 A * | 4/2000 | Sackner ............. | A41D 13/1281 600/301 |
| 6,055,448 A | 4/2000 | Anderson et al. | |
| 6,173,198 B1 | 1/2001 | Schulze et al. | |
| 6,205,346 B1 | 3/2001 | Akiva | |
| 6,285,899 B1 | 9/2001 | Ghaem et al. | |
| 6,308,093 B1 | 10/2001 | Armoundas et al. | |
| 6,327,486 B1 | 12/2001 | Nissiläet al. | |
| 6,360,119 B1 | 3/2002 | Roberts | |
| 6,381,482 B1 | 4/2002 | Jayaraman et al. | |
| 6,408,200 B1 | 6/2002 | Takashina | |
| 6,415,169 B1 * | 7/2002 | Kornrumpf ........ | A61B 5/04085 600/382 |
| 6,434,410 B1 | 8/2002 | Cordero et al. | |
| 6,532,379 B2 | 3/2003 | Stratbucker | |
| 6,553,247 B1 | 4/2003 | Rytky | |
| 6,564,079 B1 | 5/2003 | Cory et al. | |
| 6,571,115 B2 | 5/2003 | Axelgaard et al. | |
| 6,594,519 B2 | 7/2003 | Stoycos et al. | |
| 6,611,705 B2 | 8/2003 | Hopman et al. | |
| 6,687,523 B1 | 2/2004 | Jayaramen et al. | |
| 6,745,062 B1 | 6/2004 | Finneran et al. | |
| 6,748,256 B2 | 6/2004 | Brodnick et al. | |
| 6,755,795 B2 | 6/2004 | Marmaropoulos et al. | |
| 6,775,566 B2 | 8/2004 | Nissilä | |
| 6,847,836 B1 | 1/2005 | Sujdak | |
| 6,970,731 B1 | 11/2005 | Jayaraman et al. | |
| 6,973,344 B2 | 12/2005 | Finneran et al. | |
| 7,043,292 B2 | 5/2006 | Tarjan et al. | |
| 7,127,279 B2 | 10/2006 | Finneran et al. | |
| 7,154,071 B2 | 12/2006 | Sattler et al. | |
| 7,173,437 B2 | 2/2007 | Hervieux et al. | |
| 7,206,630 B1 | 4/2007 | Tarler | |
| 7,211,053 B2 | 5/2007 | Marmaropoulos et al. | |
| 7,299,084 B1 | 11/2007 | Price | |
| 8,818,478 B2 * | 8/2014 | Scheffler ............. | A41D 1/002 600/388 |
| 2003/0018251 A1 * | 1/2003 | Solomon ............ | A61B 5/04011 600/427 |
| 2003/0105403 A1 * | 6/2003 | Istvan .................. | A61B 5/0006 600/509 |
| 2003/0120163 A1 * | 6/2003 | Rudy ................. | A61B 5/04085 600/509 |
| 2004/0015194 A1 | 1/2004 | Ransbury et al. | |
| 2004/0073127 A1 * | 4/2004 | Istvan .................. | A61B 5/0006 600/513 |
| 2004/0176674 A1 * | 9/2004 | Nazeri ................ | A61B 5/0006 600/382 |
| 2004/0243204 A1 * | 12/2004 | Maghribi .............. | A61N 1/05 607/115 |
| 2004/0243205 A1 | 12/2004 | Keravel et al. | |
| 2007/0055336 A1 | 3/2007 | Greenberg et al. | |
| 2007/0073131 A1 | 3/2007 | Ryu et al. | |
| 2007/0078324 A1 | 4/2007 | Wijisiriwardana | |
| 2007/0299471 A1 | 12/2007 | Takahashi et al. | |
| 2008/0177168 A1 * | 7/2008 | Callahan ............ | A61B 5/04085 600/382 |
| 2008/0287770 A1 * | 11/2008 | Kurzweil ............ | A61B 5/0408 600/388 |
| 2008/0312522 A1 * | 12/2008 | Rowlandson ...... | A61B 5/04085 600/382 |
| 2010/0041974 A1 | 2/2010 | Ting et al. | |
| 2011/0016649 A1 | 1/2011 | Reggio et al. | |
| 2015/0231403 A1 * | 8/2015 | Kaib .................... | A61N 1/3968 607/7 |

FOREIGN PATENT DOCUMENTS

| | | |
|---|---|---|
| EP | 2105089 A1 | 9/2009 |
| EP | 2 196 142 A1 | 6/2010 |
| EP | 1 054 621 81 | 8/2010 |
| EP | 2 305 110 A1 | 4/2011 |
| EP | 2 324 761 A2 | 5/2011 |
| WO | WO 2006/095279 A1 | 9/2006 |
| WO | 2008092098 A2 | 7/2008 |
| WO | 2010054352 A1 | 5/2010 |

OTHER PUBLICATIONS

International Search Report—3 pgs., Aug. 20, 2012, CardioInsight Technologies, Inc.
Written Search Report—3 pg.s, Aug. 20, 2012, CardioInsight Technologies, Inc.

* cited by examiner

MULTI-LAYERED SENSOR APPARATUS

RELATED APPLICATION

This application is a U.S. National Stage Application filed under 35 U.S.C. §371 of PCT/US2011/066796, having a filing date of Dec. 22, 2011, which claims the benefit of U.S. Provisional Patent application Ser. No. 61/426,143, filed on Dec. 22, 2010, and entitled SENSOR ARRAY APPARATUS AND ASSOCIATED METHODS OF MAKING AND USING SAME. The entire contents of each of the above-identified patent applications are incorporated herein by reference.

TECHNICAL FIELD

This disclosure relates to sensing electrical activity, and more particularly to a multi-layered sensor apparatus.

BACKGROUND

Various electrophysiology techniques have been developed for collecting electrophysiology data for a patient. Invasive measurement techniques typically involve placing one or more electrodes into contact with biological tissue. For example, an electrophysiology catheter or probe contains one or more electrodes at its distal end, each electrode being able to record electrical activity at the location of said electrode. Thus, by placing the catheter at a particular location relative to a patient's organ, such as the heart, organ-specific electrical activity can be recorded. Sensors can also be arranged on a body surface of a patient for non-invasive acquisition of electrical information. Signal processing, such as filtering, can be applied on any such signal to remove noise or otherwise enhance the acquired electrical signals.

SUMMARY

This disclosure relates to sensing electrical activity, and more particularly to a multi-layered sensor apparatus.

In one example, the sensor apparatus can include a first substrate layer of a flexible material and a plurality of electrodes disposed on a contact surface of the first substrate layer. Electrically conductive paths are disposed on the contact surface of the first substrate layer and extend from each of the electrodes to which it is connected and terminate in a corresponding terminal end. The apparatus can also include a second substrate layer of a stretchable and conformable material. The first substrate layer is affixed to the second substrate layer and configured, such that spaced apart and interconnected portions of the first substrate layer, which include the electrodes, stretch and conform commensurate with movement of the second substrate layer.

In another example, a sensor apparatus can include an electrode carrying layer of a flexible material. The electrode carrying layer includes a plurality of loop portions of the flexible material, each loop portion having a first end connected to a base strip of the flexible material and extending from the first end along an arcuate path and terminating in a second end connected to the base strip spaced apart from the first end. A plurality of electrodes are disposed on a contact surface of the electrode carrying layer and distributed along each of the plurality of loop portions such that the electrodes in each of the plurality of loop portions move commensurate with movement of the electrode carrying layer. A plurality of electrically conductive paths electrically extend from a respective electrode and terminate at a terminal end of the electrically conductive path. Terminal ends for electrodes of one or more of the plurality of loop portions can be located at a common connector.

DETAILED DESCRIPTION

This disclosure relates to an apparatus and system for sensing electrical activity of a patient. The sensor apparatus can be provided in the form of a conformable electrode vest. This disclosure also provides a method of making the electrode vest, which can include a multi-layered arrangement of substrates and electrical circuitry. The sensor apparatus disclosed herein can be used for electrophysiology purposes. In many of the examples disclosed herein, the sensor apparatus is demonstrated as being configured for electrocardiography. In other examples, the sensor apparatus and associated system can be utilized for other types of electrophysiology, including electroencephalography, electrocorticography, electromyography, electrooculography, electroretinography, electroantennography and audiology.

Figure 1:
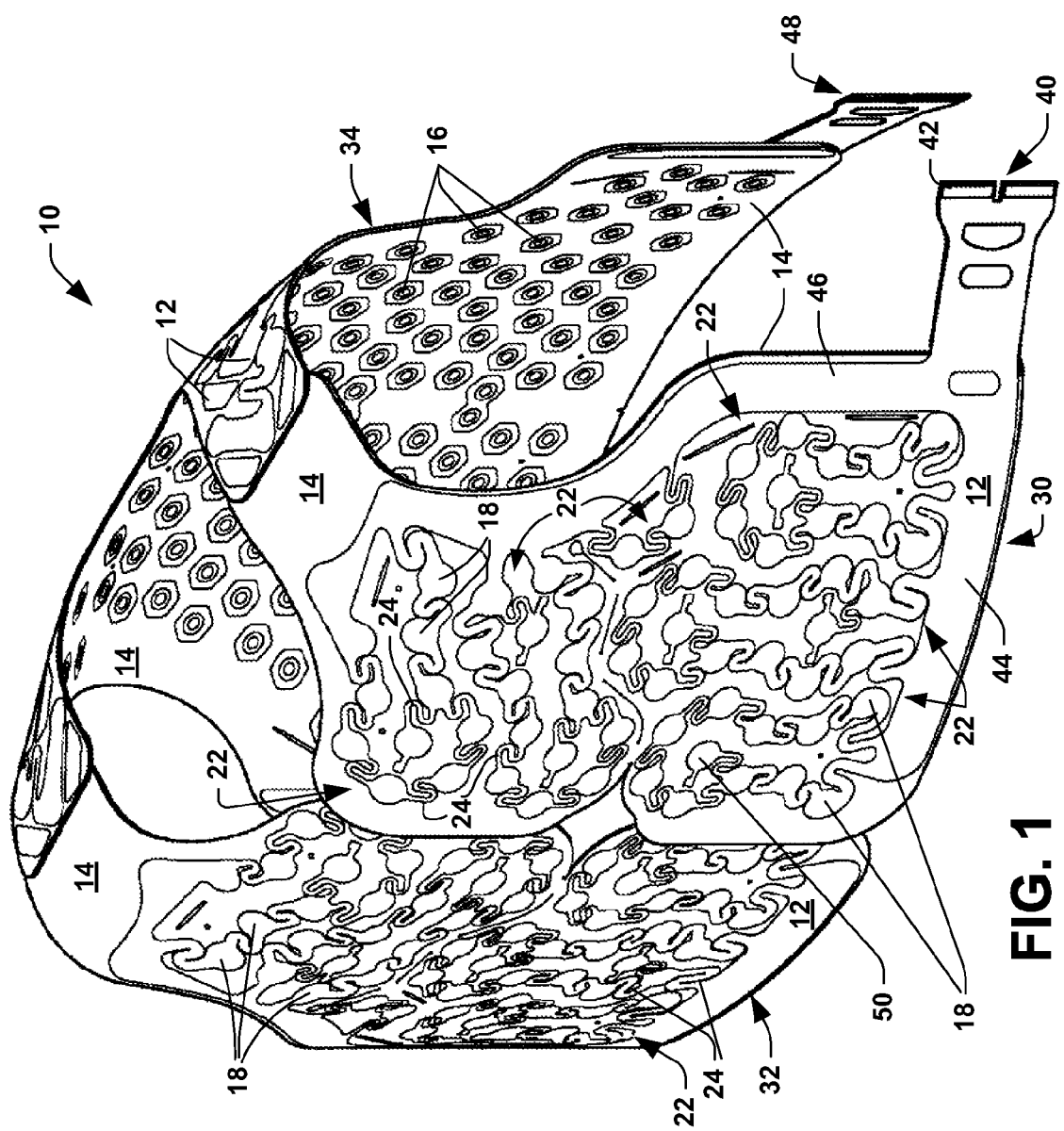
FIG. 1 depicts an example of a sensor apparatus that can be utilized for sensing electrical activity on a surface of a patient's torso.

FIG. 1 depicts an example of a sensor apparatus 10. The example sensor apparatus 10 is dimensioned and configured to be applied to a torso of a patient (e.g., a human patient); however, different configurations can be utilized depending on the patient (e.g., could be human or other animal) and the particular type of electrophysiology to be performed. The sensor apparatus 10 can come in a plurality of sizes to accommodate a range of patient's sizes and body types.

The sensor apparatus 10 includes a substrate layer 12 that is formed of a flexible material. The flexible layer 12 provides an electrode-carrying substrate layer. The flexible substrate layer 12 can be formed of a pliant flexible material such as a plastic, a polymer (e.g., a polyester, such as polyethylene terephthalate (PET)). The substrate layer 12 can be formed from a substantially planar sheet of flexible material that can bend and/or twist in directions transverse from its planar configuration. The flexible layer 12 also provides sufficient structure to maintain a general dimensions and configuration of each the sensor apparatus 10. The flexible substrate layer 12 can be mounted to another substrate layer 14 of an elastic and conformable material. The flexible layer 12 layer tends not to be stretchy as the elastic conformable layer 14 since it operates as a substrate that carries electrical circuitry. The particular configuration and of the various electrode receiving portions and connecting elements that form the flexible substrate layer 12 can be implemented by laser cutting a planar sheet of the flexible material (e.g., via automated or robotic methods). In other examples, the flexible substrate layer 12 and layer 14 can be implemented as a single layer (e.g., a conformable panel) with the circuitry printed directly on the contact surface thereof to provide a sensor apparatus.

The elastic conformable layer 14 can be a stretchable material, such as a woven or non-woven fabric material that exhibits high elasticity, such as spandex or elastane, although other elastic panels of conformable material can be utilized (e.g., similar to that used in some athletic clothing). The stretchable fabric layer can be formed of a synthetic, natural or combination of synthetic and natural materials. The stretchable fabric layer 14 allows the sections and the entire vest to be highly conformable to the patient's body shape and movements. The conformable layer 14 can exhibit an amount of stretch to maintain a maximum distance between adjacent electrodes within a predetermined distance horizontally (e.g., about 5 to 10 cm) and vertically (e.g., about 3 to 7 cm).

In some examples, the conformable layer 14 can also include one or more frangible sections (e.g., by including cuts or splits) in predetermined areas to facilitate emergency access without destroying the electrodes themselves. For instance, should electrodes need to be moved in the event of an emergency condition, such as for placing additional medical equipment (e.g., defibrillator paddles) on the patient's chest, the cuts or slits in the fabric can enable the corresponding portion of the vest to be removed from the patient's torso. Adhesive materials on and surrounding each of the electrodes 16 further can facilitate repositioning and connecting the electrodes at the appropriate locations on the patient. Additional apertures may also be provided through the conformable layer 14 to facilitate placement of electrodes on the patient, such as ECG electrodes. Additionally or alternatively, a central aperture for subxiphoid space access can be provided for emergencies and epicardial procedures during intra-procedural usage. One or both of the layers 12 and 14 can also include tangible markings or profiles designed to align with anatomical markers or locations on the patient's body to facilitate placement and application of the apparatus 10.

The flexible substrate layer 12 can be affixed to the conformable substrate layer 14 such as via an adhesive or other type of fastening means. A film adhesive can be utilized to affix the flexible substrate 12 to a panel of the conformable layer 14. As one example, the adhesive can be applied as a thin film of a TM9720, which is available from MacTec Technical Products of Stow, Ohio. By connecting the flexible substrate layer 12 to the conformable layer 14 in this or similar manner, the spaced apart and interconnected portions of the first layer, including the electrode receiving portions 18 and the electrodes disposed thereon can bend and conform to a surface of a patient's body commensurate with movement of the second substrate layer 14.

A plurality of electrodes 16 are disposed on a contact surface of corresponding electrode receiving portions of the first substrate layer 12. Each electrode 16 can operate as a sensor for detecting electrical activity and providing a corresponding electrical signal via a respective conductive trace. In the example of FIG. 1, the electrode receiving portions 18 are depicted as having a generally circular configuration, although other shapes (e.g., rectangular, oval, polygonal or the like) can be utilized in other examples. Each electrode receiving portion 18 can be dimensioned and configured to receive an electrode (or in some examples more than one electrode) on a contact surface thereof. The electrodes 16 can be applied as a coating via deposition or other methods, for example.

In the example of FIG. 1, the flexible substrate layer 12 can include one or more loops 22 of the flexible material that comprises a plurality of interconnected electrode receiving portions distributed along each loop. By providing a plurality of such loops 22, each having an arrangement of electrodes distributed along the respective loops, the sensor apparatus 10 can be provided with a substantially even spatial distribution of electrodes 16. The loops can be provided in variety of configurations, such as, for example, circular, oval, polygonal, tonsil-shaped, hourglass-shaped as well as combinations thereof.

The plurality of electrode receiving portions 18 in each of the loops 22 can be connected by a curved strip 24 of the flexible material. As one example, the curved strips 24 that interconnect each of the electrode receiving portions 18 can be implemented as a substantially S-shaped (e.g., sinusoidal or serpentine) length of the flexible material interconnected between a pair of adjacent receiving portions 18. The curved strips 24 can be implemented with other shapes, such as c-shaped, "~"-shaped, z-shaped or other curved configurations that afford some ability to provide stretchability between interconnected electrode receiving portions 18. The curved strips 24 of the flexible material layer 12 also carry one or more conductive traces the contact surface following the contour of the curved strip 24. As disclosed herein, an insulating layer and the conformable layer 14 can cover the electrical traces disposed on the substrate layer 12.

The width of the curved strips 24 can be significantly less than the diameter of each of the electrode receiving portions 18 to which they are connected. As demonstrated in the example of FIG. 1, different curved strips 24 can have different widths. The widths of each of the respective strips 24 can vary, for example, according to the number of electrical traces carried thereon as well as the dimensions of each of the electrical traces.

By configuring each of the respective loops 22 as including an arrangement of electrode receiving portions 18 and respective curved strips 24, which are attached to the conformable layer 14, the conformability and stretchability of the interconnected electrodes and electrode receiving portion of each loop is facilitated in two or more dimensions and in more than one plane. The curved strips 24 also control a maximum separation distance between adjacent electrodes connected by each strip. That is, the curved strips 24 functional operate similar to coiled springs that allow adjacent electrode receiving portions to move relatively to each other in two or more dimensions (e.g., movement toward each other and away from each other) as well as conformation to curvature in more than one plane, thereby improving the fit of the sensor apparatus 10 to a variety of differently contoured body surfaces.

The sensor apparatus 10 in the example of FIG. 1 includes a plurality of sensor array sections dimensioned and configured for placement on different portions of a patient's body surface. In the example of FIG. 1, the sensor apparatus 10 includes three sensor array sections 30, 32 and 34. For instance, each section 30, 32 and 34 can be formed of a monolithic layer (e.g., from an integral sheet) of the flexible material, each of which can be attached to a corresponding panel of the conformable layer 14.

In the example of FIG. 1, the section 30 is configured for placement on a left-side front portion of a patient's torso. The section 32 is configured for placement of a right side of a patient's torso and the section 34 is configured for placement on a back portion of a patient's torso. Collectively each of the sections 30, 32 and 34 can form a sensor vest that can be worn by a patient for holding the electrodes against the patient's skin to cover a contiguous region of the patient's torso with electrodes. Each of the sections 30, 32 and 34 can be separate sections that can be secured together via fasteners (e.g., hook and loop fasteners, straps, belts or the like). Alternatively, the sections 30, 32 and 34 can be attached to each other such as in the form of a garment that can be worn and secured to a patient's torso. In other examples, differently configured sections could cover spatially separated regions of a patient's body, which may or may not be contiguous.

Figure 2:
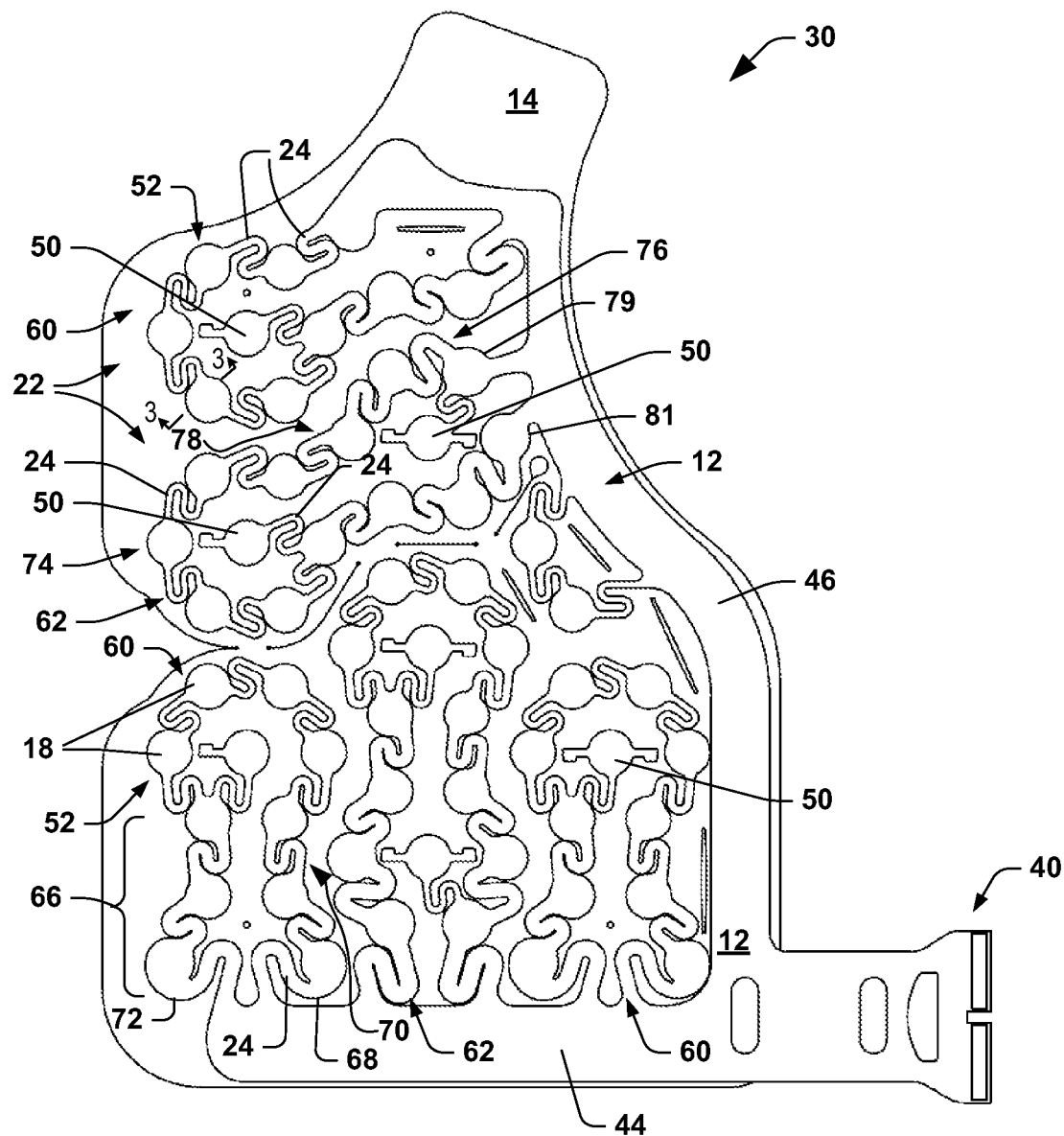
FIG. 2 depicts another example of a sensor apparatus that can be utilized for sensing electrical activity on a surface of a patient's body.

A front elevation of the left-side front section 30 is demonstrated in FIG. 2. It is to be appreciated for certain applications different numbers of electrodes and different configurations of sections can be utilized according to application requirements for a given type of electrophysiology or other purpose. In the example of FIGS. 1 and 2, the flexible layer 12, the electrodes 16 and electrical paths of the section 30 can be attached to a single common sheet of the conformable layer 14 as to define a corresponding circuit. Electrical traces electrically couple each of the electrodes 16 to terminal ends 42 of a connector 40, as shown in FIG. 1. For instance, each of the electrodes 16 in the section 30 are electrically connected with corresponding pins or terminals located at the connector 40. That is, electrical traces travel from the each of the electrodes 16 along the loops 22, to corresponding base strips 44 and 46 and then electrically connect with the terminal ends in the connector 40.

Each of the other sections 32 and 34 of the apparatus of FIG. 1 can be similarly configured. The electrodes and electrically conductive paths of the right-side section 32 can define a corresponding electrical circuit that is attached to a common second sheet of the conformable layer 14 and include a corresponding connector (not shown). Similarly, the electrodes 16 and the corresponding electrically conductive paths of the back section 34 can define another electrical circuit that is attached to a corresponding common sheet of the conformable layer 14. Each of the electrodes 16 of the back section 34 can be carried along the flexible layer 12 thereof and terminate in one or more corresponding connector portions 48. Each of the connectors 40 and 48 thus can be connected to an appropriate amplifying circuitry for recording and monitoring of the signals sensed by each of the respective electrodes 16.

As demonstrated in the example of FIGS. 1 and 2, a sensor apparatus can include multiple different configurations of the loops 22. The number of electrodes and configuration of a given loop depend on its location in the respective sections 30, 32 and 34. One or more of the loops 22 can traverse a path that provides one or more bulbous portions of the flexible material layer 12. A bulbous portion 52 can provide an open space between the bulbous looping arrangement of the flexible material layer 12 in which a central electrode receiving portion 50 is disposed. The central electrode receiving portion 50 thus carries another electrode on a contact surface thereof (not shown). The central electrode receiving portion 50 can connect to an adjacent electrode receiving portion 18 via another curved strip 24 that extends along a curved path (e.g., S-shaped path) between the interconnected electrode receiving portions.

Each bulbous portion 52 can include an arrangement of electrode receiving portions 18 disposed along a generally circular path with the central electrode receiving portion 50 located in the center thereof. The central electrode receiving portion 50 can be generally uniformly spaced apart from the other electrode receiving portions in the respective bulbous portion 52. The central electrode receiving portion 50 can be connected to a single other electrode receiving portion via its associated interconnecting curved strip 24. In this way, the central electrode receiving portion 50 seems to "float" in the center of the bulbous portion 52, although the flexible substrate layer in each loop can be affixed to the elastic conformable layer 14 as disclosed herein.

As shown in the example sensor apparatus 30 of FIG. 2, a plurality of loops 22 extend from a lateral base strip 44 and another plurality of loops 22 extend outwardly from the vertically extending base strip 46. By employing base strips 44 and 46 that are substantially transverse to each other along adjacent side edges of the sensor section, the bulk of the electrical traces for carrying electrical signals from the electrodes 16 are further distributed within such strips at the periphery of the sensor apparatus 30 such that the conformability of the sensor apparatus can be enhanced for the respective loops. Thus, not only is there additional conformability of each loop, relative movement between the respective loops commensurate with the conformability of the conformable layer 14 to the body surface is further facilitated.

In the example of FIGS. 1 and 2 (as well other figures herein), a majority of the loops 22 can be considered as having either a tonsil-shaped loop or an hourglass-shaped loop. In the example FIG. 2, the tonsil-shaped loops are demonstrated at 60 and the hourglass-shaped loops are demonstrated at 62. Each of the loops 60 and 62 is generally symmetrical about a longitudinal central axis extending through the respective loop. They can be considered "generally symmetrical" since the shapes are similar but that the sides can vary depending on its location. The trapezoidal and hourglass shaped loops can be arranged in an alternating pattern such as shown herein.

As used herein, the term 'tonsil-shaped' refers to a loop configuration that includes a bulbous loop portion 52 extending from sides of a trapezoidal shaped portion 66, such as shown FIG. 2. As one example, the tonsil-shaped loop 60 includes a first end 68 that is connected with the base strip 44 via a curved connecting strip 24 of the flexible material layer. A side portion of the trapezoidal portion 66 extends inwardly from the end 68 toward a central longitudinal axis of the loop creating an indented curved intermediate portion 70. The inwardly curved intermediate portion 70 further transitions from trapezoidal portion 66 into the bulbous portion 52 by curving outwardly from the indented portion. The curved indented portion 70 is configured with a radius of curvature configured to operate as a receptacle for receiving a corresponding mating bulbous portion of an adjacent loop (e.g., an hourglass shaped loop 62). The tonsil-shaped loop 60 continues along the path of the bulbous portion 52 by curving inwardly back towards the base strip 44 to complete the bulbous portion 52. The loop 60 then extends to provide the opposite leg of its trapezoidal portion 66 by turning outwardly from the bulbous portion 52 away from its opposing side, forming another indented portion. The second leg of its trapezoidal portion terminates in a second end 72 that is attached with the same base strip 44 yet spaced apart from the first end 68. Thus the trapezoidal portion defines intermediate tapered portions at 70 between the ends 68 and 70 of the trapezoidal portion 66 and the bulbous portion 52. In the example of FIG. 2, a single central electrode receiving portion 50 of the flexible layer 12 is located near the center of the tonsil-shaped loop 60. In other examples, the loop 60 may include more than one electrode in the central portion thereof or it may include no electrode portions located within the loop.

Additionally, as used herein, the term 'hourglass-shaped' refers to a loop configuration 62 that includes a generally hourglass (e.g., dumbbell) shape that includes a pair of bulbous portions 74 and 76 spaced apart from each other in the loop by an intermediate tapered portion 78. Referring the example of FIG. 2, an hourglass-shaped loop 62 includes a first end 79 that is attached to a corresponding base strip 46 and extends arcuately outwardly from the base strip 46 and then inwardly toward an opposing side to form a first outward curve of the bulbous portion 76. The tapered central portion provides an inward curve having a radius of curvature that is comparable to the outward curve of the bulbous portions 52. The loop 62 then curves arcuately outwardly and then inwardly back towards the base strip 56 from which it extends to provide the distal end of the loop 62. From the end, the loop curves inwardly to complete the bulbous portion 74. From the end of the bulbous portion 74, the loop curves inwardly to provide a second inward curved intermediate portion 78 between the bulbous portions 76 and 74. From the second inwardly curved intermediate portion 78, the loop turns outwardly away from the opposing side and then curves back inwardly to terminate in its second end 81, which is attached to the base strip 46 and spaced apart from the first end 79. Within the center of each bulbous portion 76 and 74 is a corresponding central electrode receiving portion 50 (similar to the tonsil-shaped portion), which is connected to an adjacent one of the electrode receiving portions by a corresponding curved (e.g., S-shaped) strip 24.

Each of the sensor apparatus sections 30, 32 and 34 can thus include an arrangement of tonsil-shaped loops and hourglass-shaped loops. The number of electrode receiving portions and the number of loops can vary according the surface area to be covered by the respective sensor apparatus. The number of electrode receiving portions and electrodes can also vary depending on the purpose for which the sensor apparatus is to be employed. These types of variations will be apparent based on the teachings herein.

As mentioned above with respect to FIG. 1, each of the sections 30, 32, and 34 can be formed of a multi layer structure that includes the conformable layer 14 and the flexible substrate layer 12 to which the corresponding electrodes are attached at a contact thereof. The conformable layer 14 can be a single sheet or a multi layered sheet of elastic conformable material that facilitates the application in conforming to the surface of a patient's body. As shown in the example of FIG. 2, the corresponding conformable layer 14 can include a plurality of slits and curved portion to mitigate tearing and to enhance its ability to conform to the patient's torso or other area to which a sensor apparatus may be utilized.

Figure 3:
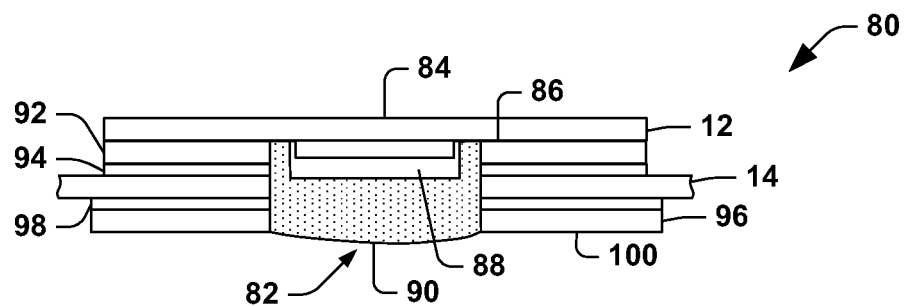
FIG. 3 is a cross sectional view of part of a sensor taken along line of 3-3 in FIG. 2.

FIG. 3 depicts an example of the sensor layers 80 taken through line 3-3 of the sensor array section 30 of FIG. 2. The line 3-3 is taken through an electrode receiving portion 18 of the flexible substrate layer 12 to further demonstrate the layers that can form an electrode structure 82. In the example of FIG. 3, the electrode structure 82 includes a first layer 84 of an electrically conductive material that is deposited onto a contact surface 86 of the substrate layer 12. A second electrode layer 88 of another electrically conductive material is deposited in an overlying relation superimposed on the first electrode layer 84. In the example of FIG. 3, the second electrode layer 88 can surround and cover the underlying first electrode layer 84. The second layer 88 can be a different conductive material from that of the first layer 84. As an example, the first electrode layer can be formed of a silver or silver alloy material. The second electrode layer can also be formed of a silver or silver alloy layer such as silver chloride (or other electrically conductive materials, such as copper, copper alloys or silver alloys to name a few). Thus, the electrodes and conductive traces can be transparent under X-ray fluoroscopy but be visible in other imaging modalities, such as computed tomography (CT) imaging or magnetic resonance imaging (MRI).

A layer 90 of an electrically conductive gel can be deposited over the exposed second electrode structures 88 of the sensor apparatus. For example, the layer 90 can be an adhesive gel that is applied to the sensor apparatus after the other layers of the apparatus have been fabricated. The layer 90 can be applied by the manufacturer (e.g., before shipping) or, alternatively, in other examples, the layer 90 can be applied prior to use (e.g., by the user). The gel layer and the electrode layers 84 and 88, individually or collectively, form the electrode structure 82 that provides an electrically conductive interface configured to contact with a body surface of the patient.

By way of example, the layer 90 can be implemented as a medical grade adhesive, such as may be of a wet gel or a solid gel construction. As an example, wet gel and solid gel materials, which can be used for the layer 90 are commercially available from Vermed, Inc. of Bellows Falls, Vt. Other medical grade electrically conductive gels and other materials may also be utilized.

An insulating layer 92 can also be provided on the contact surface 86 of the substrate layer 12 to cover the electrically conductive traces applied with the layer 84. The insulating layer can be a dielectric material having a high dielectric constant sufficient to prevent the flow of electrical current. In some examples, the insulating layer should be sufficient to withstand a 5 kV pulse. To facilitate fabrication of the sensor apparatus 10, the insulating layer 92 can be a coating that can be applied as a liquid or (e.g., via spraying, deposition, or the like) onto the contact surface 86 of the flexible substrate layer 12 and over the exposed electrically conductive traces. The insulating layer 92 can be applied to the entire contact surface 86 except where the electrode layers 84 and 88 have been applied to the substrate layer 12 and at the connector ends. A mask or other means can be utilized to prevent application of the insulating material onto the exposed electrode structures 84 and 88. By applying a high dielectric film over the electrically conductive traces that are printed on the polyester substrate, traces can converge to a close proximity of one another (e.g., with a spacing of about 0.05 inches at the connectors). Additionally, the insulating layer 92 can protect the traces and still permit sufficient flexibility for the sensor apparatus.

The elastic conformable layer 14 can be secured relative to the insulating layer 92 such as by a corresponding adhesive layer 94. In one example, the adhesive layer 94 can be applied to coat the entire flexible layer 12 (except at the electrode structures 84 and 88) to affix the flexible layer to corresponding surfaces of the elastic conformable layer 14. Alternatively, the adhesive may be applied strategically to provide for the desired fixation between the layers 12 and 14. Thus, the areas of the elastic conformable layer 14 that are not occupied by the flexible layer 12 are free to expand and contract, thereby enhancing the conformability of the resulting sensor apparatus.

A corresponding adhesive layer 96 can be applied in a circumscribing relationship around each the electrode layers 84 and 88 to facilitate secure attachment of the electrode structure 82 to a patient's body surface. For example, the adhesive layer 96 can be in the form of an annular ring of a foam or fabric material that surrounds each the electrode structure 82. For example, the layer 96 can be secured to the elastic conformable layer 14 via an appropriate adhesive layer 98. The adhesive layer 98 can be formed as an integral part of the layer 96 itself or be applied separately. Alternatively, the annular ring can formed from a sheet of a material having one side surface 100 containing a medical grade adhesive while the other side can be initially free of adhesive, but can be affixed to the contact surface side of the elastic polymer layer by applying an adhesive layer 98. The adhesive can be the same adhesive that is used to affix the polyester layer to the stretchable fabric layer or it can be different. The electrode gel layer 90 and the adhesive at the surface 100 of the layer 96 cooperate to hold the electrodes at a desired location when the sensor apparatus is attached to the patient's body surface.

As one example, the adhesive layer 96 of material that is applied around each electrode structure 82 can be implemented as a semi-interpenetrating polymer network, such as shown and described in U.S. Pat. No. 5,980,923 which is incorporated herein by reference. For example, the ring of material can made from a fabric or foam material product, such as a non-woven silicone adhesive material that is commercially available from Bio Med Sciences, Inc. of Allentown, Pa. Other non-woven or woven fabrics or foam materials can also be utilized.

Even in circumstances where the bond between the patient's skin and the adhesive gel applied over the electrode may tend to release, the additional adhesion afforded by the fabric ring structure surrounding the electrode can help maintain electrical contact between the electrode structure 82 and the patient's body surface. The use of such an adhesive material in conjunction with the electrically conductive adhesive gel that is applied over the electrode thus can afford advantages in maintaining electrical contact between a given electrode and the patient in a variety of environmental conditions including sweating by the patient.

During the manufacture of a given section of the sensor apparatus, the layer (e.g., a soft pliant annular ring) 96 that is applied around the electrode layers 84 an 88 can also operate as a well (e.g., receptacle) in which the adhesive gel layer can be applied and coated over the electrode layers 84 and 88. Thus, the adhesive fabric that is applied around the electrodes serves a dual purpose; namely, facilitating manufacture by providing a structure to hold the adhesive gel that is being applied as well as itself promotes adhesion to the patient's skin when the vest is in use.

Figure 4:
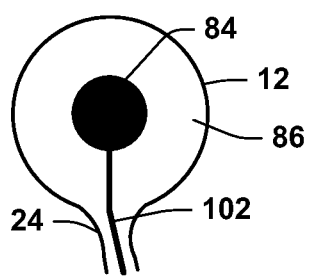
FIG. 4 depicts an enlarged view of an example of a first electrically conductive layer.

FIGS. 4, 5, 6 and 7 demonstrate further examples of different layers in the layered structure 80 of FIG. 3. In the example of FIG. 4, the first electrode layer 84 is deposited on the contact surface 86 of the flexible layer 12. The electrode layer 84 can be applied over the center of the electrode receiving portion. An electrically conductive trace 102 extends from the electrode 84 through a corresponding connector strip 24, such as may connect the electrode receiving portion of the layer 12 with another electrode receiving portion or a corresponding base strip thereof. Other electrically conductive traces (not shown) can pass along a periphery of the electrode receiving portion (see, e.g., FIG. 8).

Figure 5:
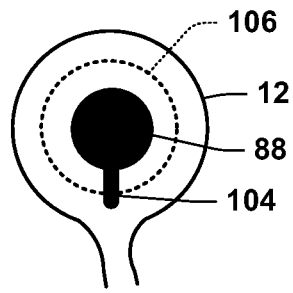
FIG. 5 depicts an enlarged view of an example of another electrically conductive layer that can be applied over the layer of FIG. 4.

In the example of FIG. 5, the second electrode layer 88 is shown, such as can be applied over the first electrode layer 84. A corresponding projection 104 of the electrically conductive material (e.g., silver chloride) extends radially outwardly from the central electrode structure 88 such as to cover a portion of the electrical trace 102 that is part of the electrode layer 84. A dashed line 106 demonstrates an inner periphery of an insulating layer (e.g., insulating layer 92 of FIG. 3).

Figure 6:
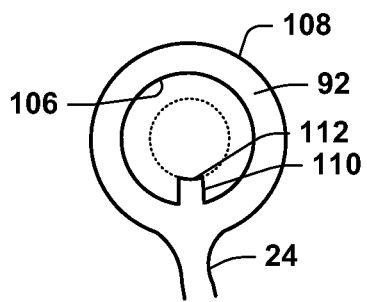
FIG. 6 is an enlarged view of an insulating layer that can be applied to a substrate over electrical traces.

FIG. 6 depicts an example a configuration of the insulating layer 92 that can be applied to the contact surface of the flexible layer 12. In the example of FIG. 6, the insulating layer 92 has an outer edge that conforms to the outer edge of the flexible layer 12, including passing along to a corresponding curved connecting strip 24 that extends outwardly from the electrical receiving portion. The insulating layer 92 also includes an inner periphery 106 that is spaced radially inwardly from the outer edge 108 thereof. A corresponding projection 110 of the insulating layer extends radially inwardly from the inner periphery 106 aligned with the electrically conductive projection 104 (FIG. 5) towards a center of the electrode receiving portion. For example, the projection 110 can extend radially inwardly from the inner periphery 106 to terminate in an end 112 that is aligned with the outer periphery of the first or second electrode layers 84, 88. Thus, the insulating layer 92 and the projection 110 thereof can cover the electrode projection 104 and the surrounding contact surface of the flexible layer 12.

Figure 7:
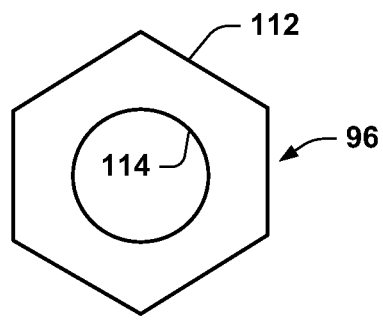
FIG. 7 is an enlarged view of an adhesive pad that can be applied around an electrode.

FIG. 7 depicts an example of an electrode pad 96 that can be applied in a circumscribing relationship relative to the electrodes 84 and 88 of a sensor apparatus. In the example of FIG. 7 the electrode pad 96 has a hexagonal outer edge 112 and a circular inner periphery 114. The inner periphery 114 can be dimensioned and configured to match the radius of the inner periphery 106 of the insulating layer 92. While the inner periphery and outer edge 112 are demonstrated with particular shapes, it is to be understood and appreciated that other configurations can be utilized for the layer 96.

FIGS. 8-15 depict examples of layers that can be utilized to form a sensor apparatus the context of the left-front section 30 of a sensor apparatus. Each of the other sections 32 and 34 of the sensor apparatus 10 of FIG. 1 as well as other configurations of sensor apparatuses can be implemented using a similar arrangement of layers based on the teachings herein. In the examples of FIGS. 8-15, each of the respective layers is shown in relation to the configuration of the flexible substrate layer. However, it is to be understood that the respective layers (other than the electrically conductive layer of FIG. 8) may not be applied directly to the substrate layers but instead may arranged in a layered construction similar to as shown and described herein such as with respect to FIG. 3. That is, the layers are being shown in FIGS. 9-15 on the flexible substrate layer for purposes of simplicity of illustration and explanation as to demonstrate their relative position with respect to configuration the flexible substrate layer.

Figure 8:
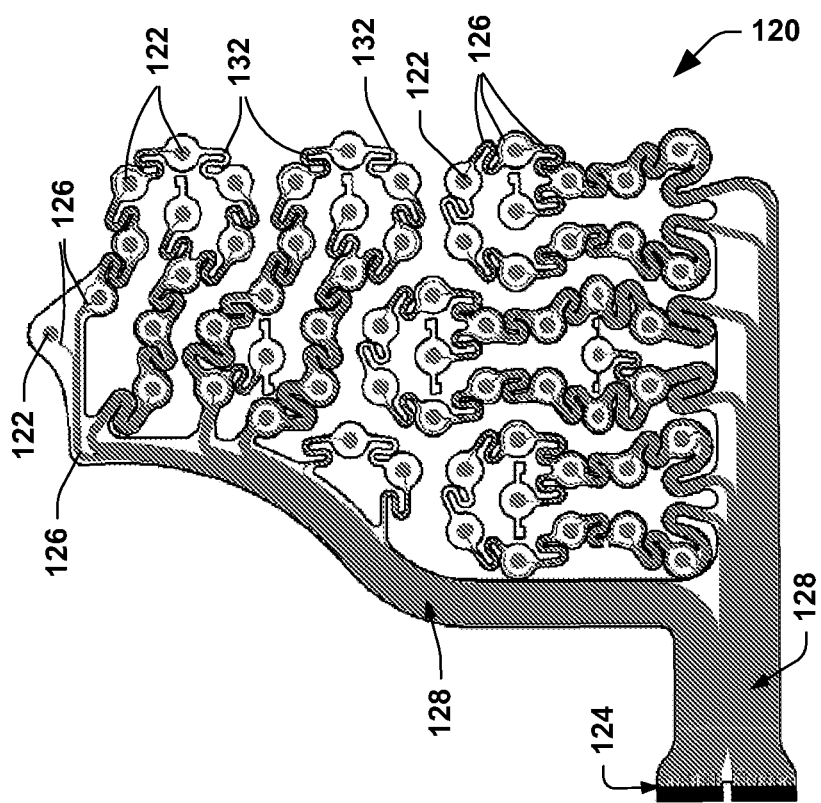
FIG. 8 depicts an example of an electrically conductive layer for the sensor apparatus of FIG. 2.

FIG. 8 depicts an example of an electrode layer 120 that can be applied to a contact surface of a flexible layer (e.g., the layer 12 of FIGS. 1-3). The electrode layer 120 includes a distributed arrangement of electrodes and corresponding electrically conductive traces. The traces that extend from each electrode 122 to terminate in a corresponding end at a terminal connector demonstrated at 124. Each of the respective traces can be electrically separate from each other. The layer 120 can be formed, for example, of silver or a silver compound or other material (e.g., copper, alloy, electrically conductive ink or the like).

Figure 10:
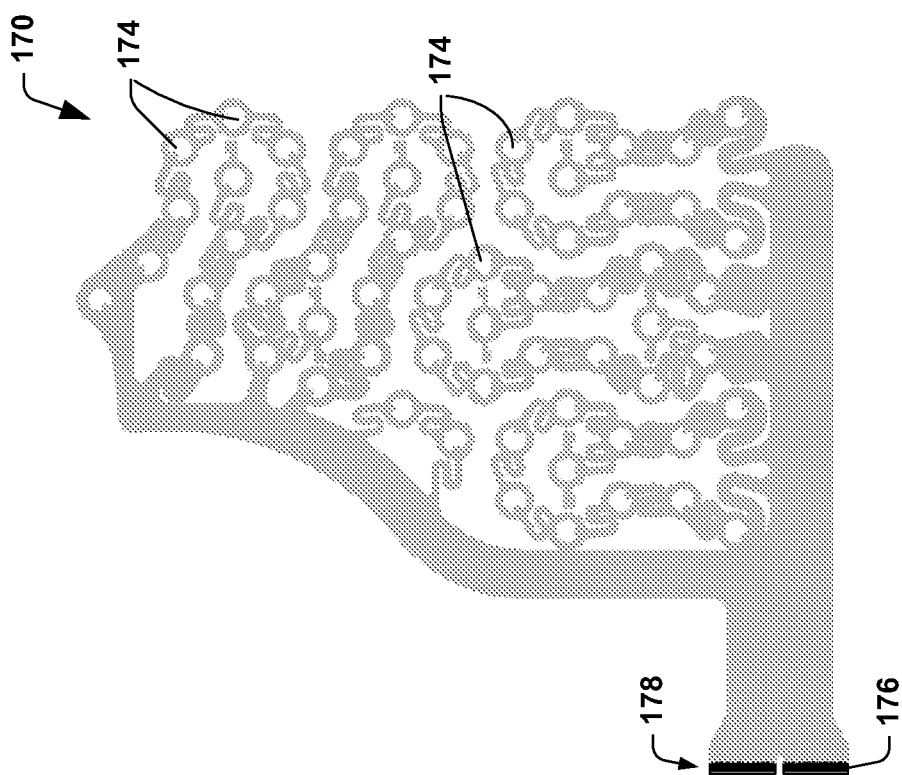
FIG. 10 depicts an example of an insulating layer that can be applied to a substrate in the sensor apparatus of FIG. 2.

Electrical isolation of each of the respective electrical traces 126 can be facilitated and maintained by applying a corresponding insulating layer over the conductive traces, such as disclosed with respect to FIG. 10. It is noted that the electrical traces 126 for a sensor apparatus can extend from respective electrodes toward a common connector (or to plural connectors) feed together in an additive manner, such as to result in all of the traces terminating in the connector end 124. Similarly, the electrical traces associated with each corresponding loop can accumulate from a corresponding distal end of the loop (distal from a respective base strip) and increase in number as the conductor passes each next electrode structure.

In the example of FIG. 8, adjacent pair electrodes 122 of each of the loop, such as at the distal-most end, can be connected to each other by a corresponding curved portion 132 with no electrically conductive trace on such curved portion 132. Instead, in this example, the electrical traces extend from the distal end electrodes 122 through the path of the loop to accumulate at a corresponding base strip portion 128 where they feed to the connector end 124. For instance, as an electrically conductive trace passes through a corresponding electrode receiving portion of a given loop, the trace can pass near the periphery over one of the sides of the periphery to extend spaced apart from and around the electrode that is applied at such electrode receiving portions. In this way, electrode receiving portions closer to the base strip 128 have a greater number of traces surrounding the electrode than traces near the electrodes 122.

Figure 9:
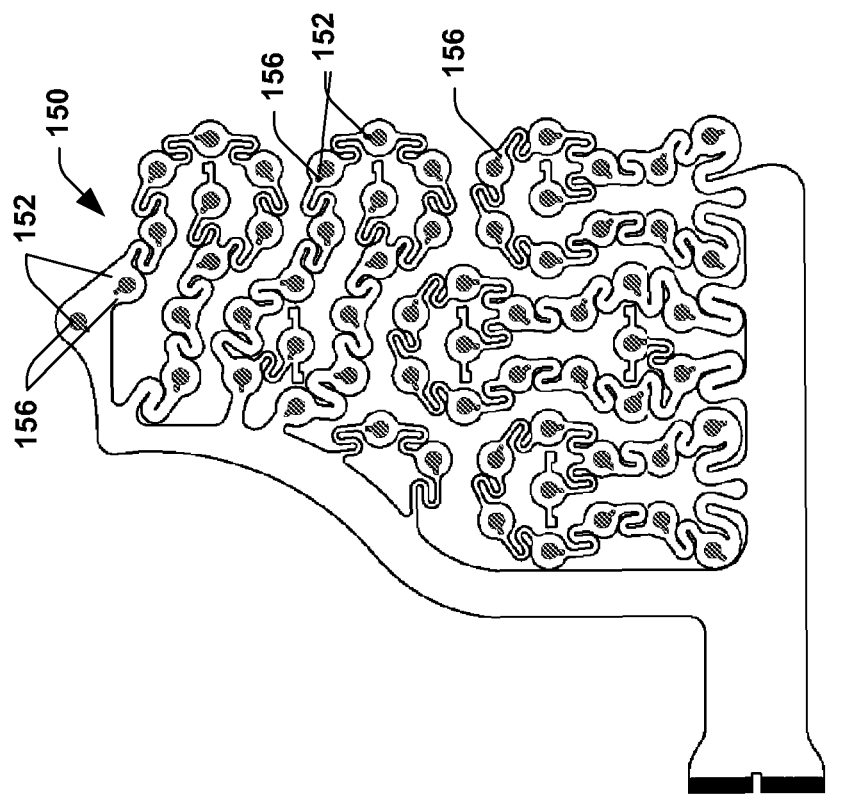
FIG. 9 depicts an example of another electrode layer that for the sensor apparatus of FIG. 2.

FIG. 9 depicts an example of a second electrode layer 150. The electrode layer 150 can correspond to the layer 88 shown and disclosed with respect to FIGS. 3 and 5. In the example of FIG. 9, the electrode layer 150 includes a plurality of electrically conductive structures 152 that are aligned with the electrode structure 122 of FIG. 8. The electrically conductive structures can have a diameter that is slightly greater than the electrode structures in FIG. 8 and be positioned at a center of each electrode receiving portion of the flexible layer 154 as to overly the first electrode layer. Each electrode structure 152 also includes a corresponding projection 156 that extends radially outwardly along the flexible substrate. For example, each projection 156 extends in a direction that is aligned with a corresponding electrical trace from the first electrode layer 120 of FIG. 8. In this way, when the electrode layer 150 is applied over the electrode layer 120 the projections 156 cover a portion of the electrical trace adjacent to the electrode from which it extends.

FIG. 10 depicts an example of an insulating layer 170. The insulating layer 170 is formed of an electrically insulating material that can be applied over the electrically conductive layers 120 and 150 of FIGS. 8 and 9, respectively. The electrically conductive layer 170 can be applied as a single coating of a high dielectric material, such as a flexible ultraviolet cured dielectric material (e.g., a coating). The insulating layer 170, as shown in the example of FIG. 10, covers substantially the entire contact surface of the flexible substrate layer except for apertures aligned with each of the electrode structures. Additionally, as shown in the example of FIG. 6, the insulating layer 170 includes a projection that extends over at least a substantial portion of the projection 156 (e.g., the entire projection) of the second electrode layer 150. Pins 176 of the electrically conductive layer 120 (FIG. 8) at the terminal connector 178 also remain free of the insulating layer to facilitate connection with other circuitry. An insulating pitch flex connector can be utilized to separate each of the pins 178 from each other by the high dielectric wall (e.g., of a plastic material) that can extend through and penetrate the polyester substrate on which the electrical traces are printed. Thus, the housing of the connector 176 formed of a high dielectric material, such as an electrically isolating polymer, can electrically isolate each of the exposed traces on the tail end of the connectors. The central apertures 174, which are free of the insulating material, are aligned axially with the electrode layers such that the electrode structures remain exposed through the insulating layer.

Figure 11:
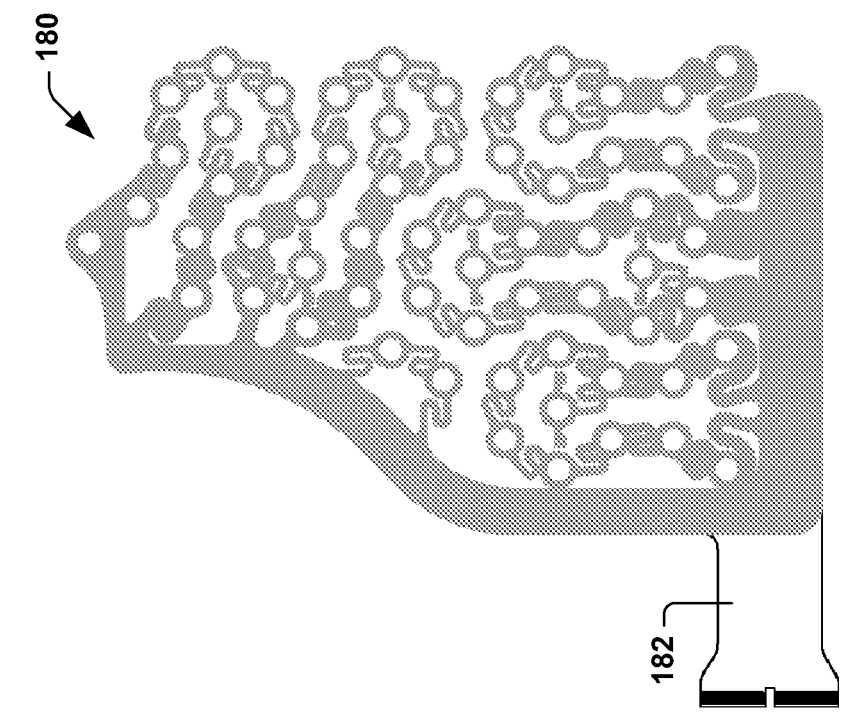
FIG. 11 depicts an example of an adhesive layer for the sensor apparatus of FIG. 2.
Figure 12:
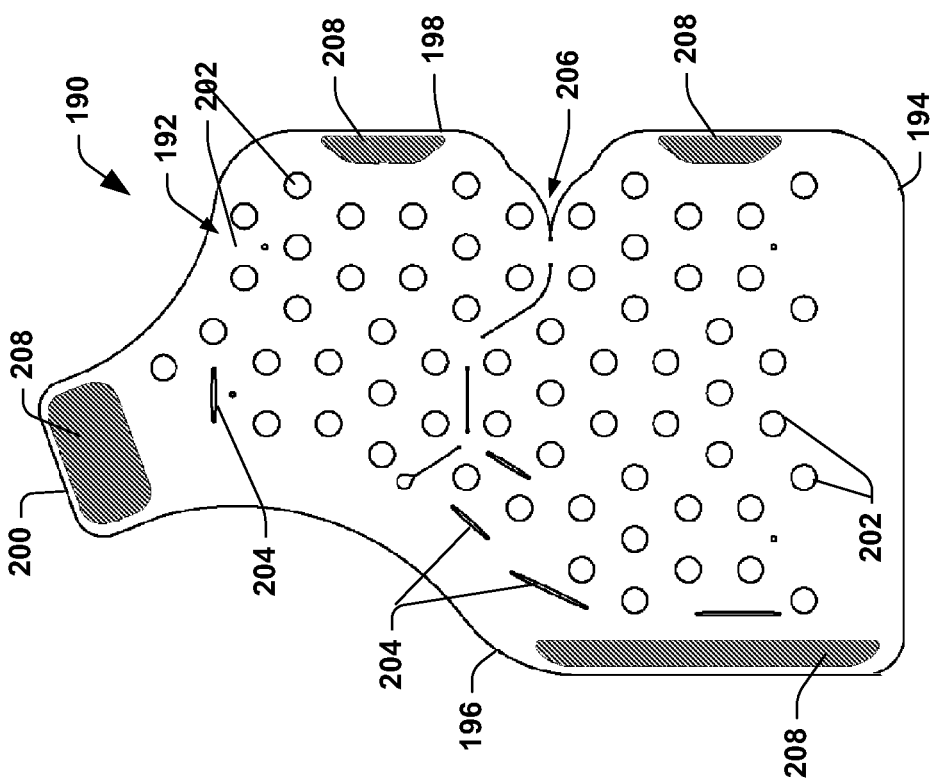
FIG. 12 depicts an example of a conformable layer can be utilized in the sensor apparatus of FIG. 2.

FIG. 11 demonstrates an example of an adhesive layer 180 that can be applied for attaching the preceding layers, such as the electrode layers 120 and 150 and the dielectric layer as well as the corresponding flexible substrate layer, to the conformable elastic layer (e.g., layer 14 of FIGS. 1-3 and also shown in FIG. 12). The adhesive layer 180 can be applied over the insulating layer 170, for example, except along the base strip portion of the terminal connector 182. Those skilled in the art will appreciate various types of adhesives that can be utilized to afford sufficient flexibility and conformability of the sensor apparatus, such as disclosed herein.

FIG. 12 depicts an example of an elastic conformable layer 190 such as corresponding to the elastic conformable layer 14 of FIGS. 1-3. In the example of FIG. 12, the elastic conformable layer 190 can be formed of a sheet of an elastic material, such as can be a woven or non-woven elastic fabric. The sheet 192 is dimensioned and configured for application and attachment to the flexible substrate layer onto which the corresponding layers of FIGS. 8-11 have been applied. The sheet 192 includes a base edge 194. Corresponding side edges 196 and 198 that extend outwardly from the base edge 194 to terminate in the corresponding distal end 200. In this example, the side edges can taper together proximal the end 200 to form a narrow extension (e.g., a shoulder portion) that terminates in the distal end 200.

The sheet 192 also includes a plurality of apertures 202 formed through (e.g., by cutting or otherwise removing a portion of the sheet). Each of the respective apertures 202 can be aligned with corresponding electrodes such that when the sheet is applied to the flexible substrate layer, the electrode layers 120 and/or 150 the central portions of the electrodes remains exposed through the apertures 202. However, the corresponding insulating layer 170 and adhesive 180 can remain covered by the sheet 192 of the conformable layer 190. A plurality of cuts or slits 204 can be formed through the sheet, such as at locations that are not aligned with the flexible substrate layer but instead correspond to open spaces such as within loops or between adjacent loops. The cuts and slits further facilitate expansion and contraction of the conformable layer 190 and the entire sensor apparatus. The corresponding slits 204 also provide for strain relief to prevent tearing of the sheet 192 when the sensor apparatus is applied to the patient.

To further facilitate conformability of the conformable layer 190 and the structures that are attached thereto, the side edge 198 includes an indentation at an intermediate portion thereof to facilitate positioning and conformability of each of the portions on opposing sides of the intermediate indented portion 206. Additionally, since in certain examples the apparatus can be utilized in conjunction with other sections of sensor apparatuses (e.g., see FIG. 1), fastener portions 208 can be applied to the sheet 192 near edges for attachment to other sensor apparatus sections. For example, the fasteners 208 can be hook or loop type fasteners. Other types of fasteners can also be utilized, such as straps, belts or the like.

Figure 13:
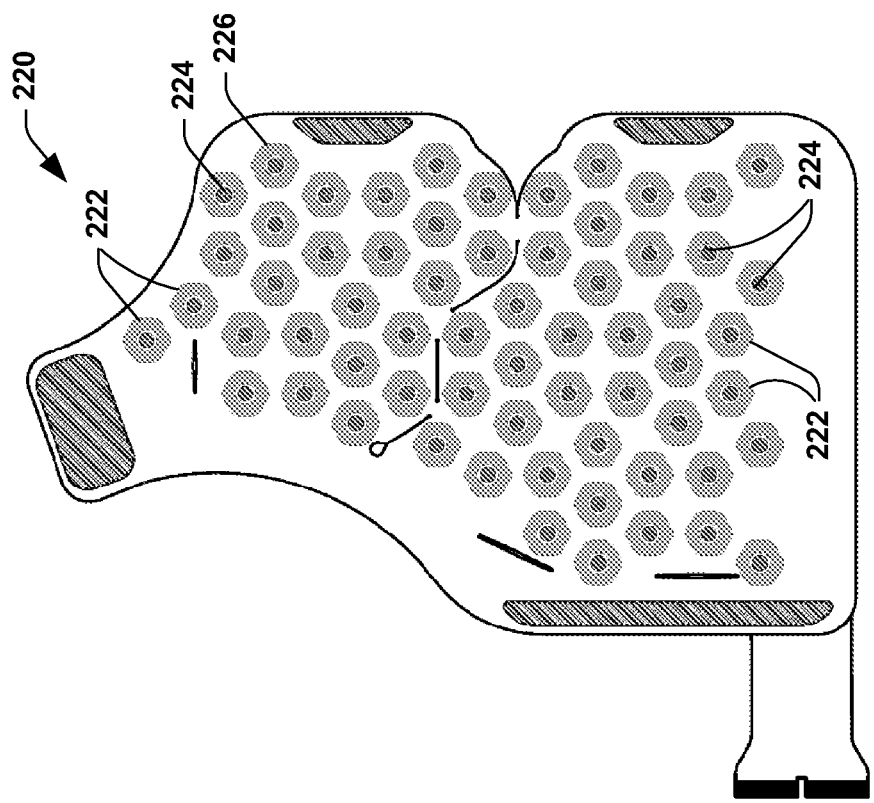
FIG. 13 depicts an example of adhesive pads that can be applied around electrodes for the sensor apparatus of FIG. 2.

FIG. 13 depicts an example of an adhesive layer that can be applied to the contact surface of the elastic conformable layer 190 of FIG. 12. The pad layer 220 can include a plurality of electrode pads 222. Each of the pads 222 can be implemented as a generally angular ring having an inner periphery 224 and an outer periphery 226. The inner periphery can be dimensioned and configured to correspond to the dimensions and configurations of the aperture 202 through the sheet 192 of FIG. 12. In this way each of the pads 222 when applied to the contact surface of the sheet 192 of the sensor apparatus help hold each of the electrode structures in place and in contact with the body surface of a patient. As mentioned above, the pads 222 can also provide a well (e.g., a receptacle) for receiving an electrically conductive gel therein over the electrode structures.

Each of the pads 222 can be formed of an electrically insulating material such as a foam or fabric. For example, the pads 222 can be implemented as a double sided foam material, such as a medical grade adhesive foam that includes adhesive on both surfaces.

In addition to constructing the skin side surface as disclosed herein, graphics and other markings can be applied to the non-contact surface of the flexible substrate layer. Examples of such markings and graphics are demonstrated in the examples of FIGS. 14 and 15. The configuration of FIGS. 14-15 appears to be a mirror image of the examples demonstrated in FIGS. 8-13. However, it is re-iterated that the surface shown in FIGS. 14 and 15 is the opposite surface from FIGS. 8-13 (e.g., it is the non-contact surface that is visible when the sensor apparatus is applied to a patient).

Figure 14:
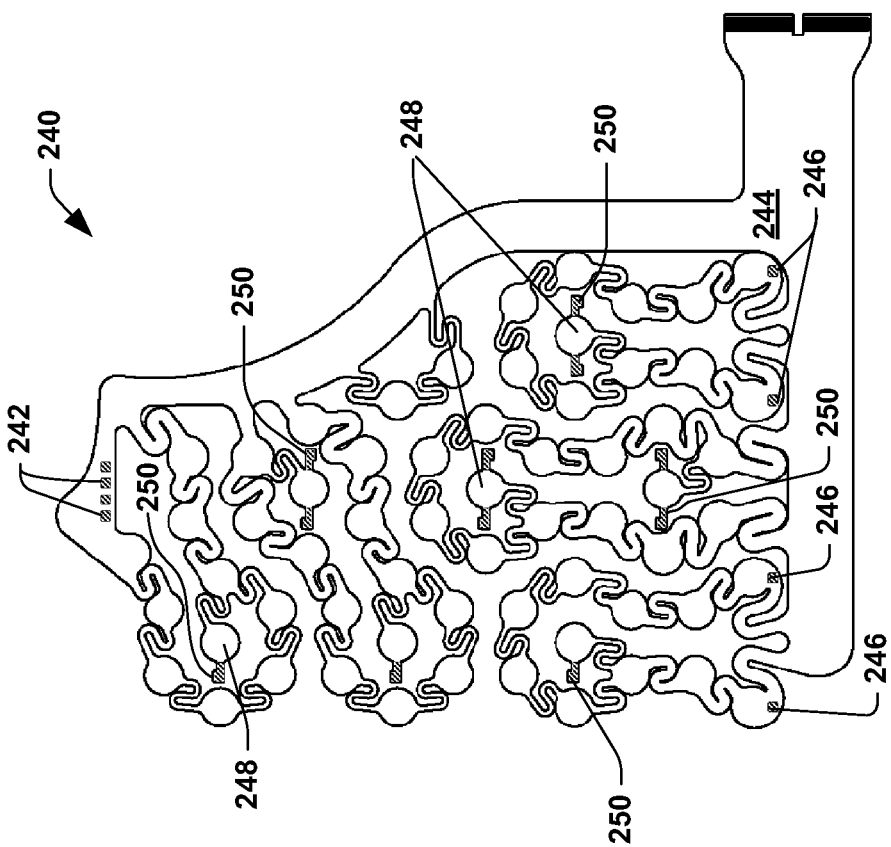
FIG. 14 depicts an example of marking layers that can be applied to a substrate for the sensor apparatus of FIG. 2.

FIG. 14 demonstrates an example of a flexible substrate layer 240 illustrated from the non-contact surface 244 thereof. In the example of FIG. 14, a set of radio opaque markings 242 are applied to the non-contact surface 244 of the substrate layer 240. For example a set of markings can be applied near a top end as indicated at 242 as well as markings adjacent a bottom end demonstrated at 246. Central electrode receiving portions 248 of the respective loops of the flexible material layer can also include projections 250 to which markings can also be applied. For example, the markings at 242, 246 and 250 can be implemented as a coating of silver or silver chloride (e.g., similar to the conductive silver material utilized for the first electrode structure), such as can be a conductive ink or other radio opaque material.

Figure 15:
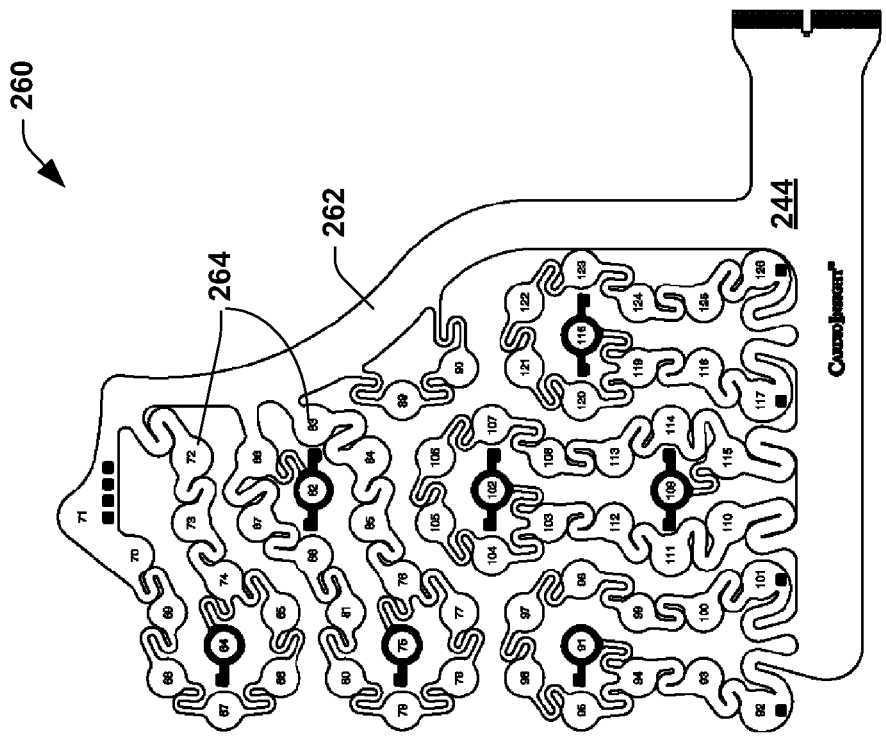
FIG. 15 depicts an example of graphics and other markings that can be applied over the marking layer of FIG. 14.

FIG. 15 demonstrates an example of a graphic layer 260 that can be applied to the non-contact surface 244 of a flexible substrate layer 262. In the example of FIG. 15, graphics 264 are applied to each of the electrode receiving portions, such as to identify a number or other designator for uniquely visually identifying each of the electrodes. The graphic identifiers (e.g., numbers) can be coordinated with associated electronics to identify relationships between signals and physical locations, such may be used to facilitate identifying bad connections, if any. Additional graphics can also be applied over the conductive markers at 242, 246 and 250 of FIG. 14, such as to protect the electrically conductive layer as well as to render it more identifiable to the user.

From the example of FIGS. 8-16, a sensor apparatus (e.g., for the sensor section 30 of FIGS. 1 and 2) can be constructed by fabricating the apparatus to have a combination of the layers as shown and described. For instance, starting from the contact side of the flexible substrate, the layer 120 can be applied to the substrate. The next conductive layer 150 can be applied over the layer 120. The insulating layer 170 can be applied over the electrically conductive layers 120 and 150. The adhesive layer can be applied over the insulating layer to attach the structure to the elastic conformable layer 190. The adhesive layer (e.g., pads) 220 can be applied to the conformable layer 190 around the apertures. On the non-contact side, the layers 240 and 260 can be applied. A similar construction can be implemented for other configurations of sensor apparatuses, including sensor sections 32 and 34 of FIG. 1.

Figure 16:
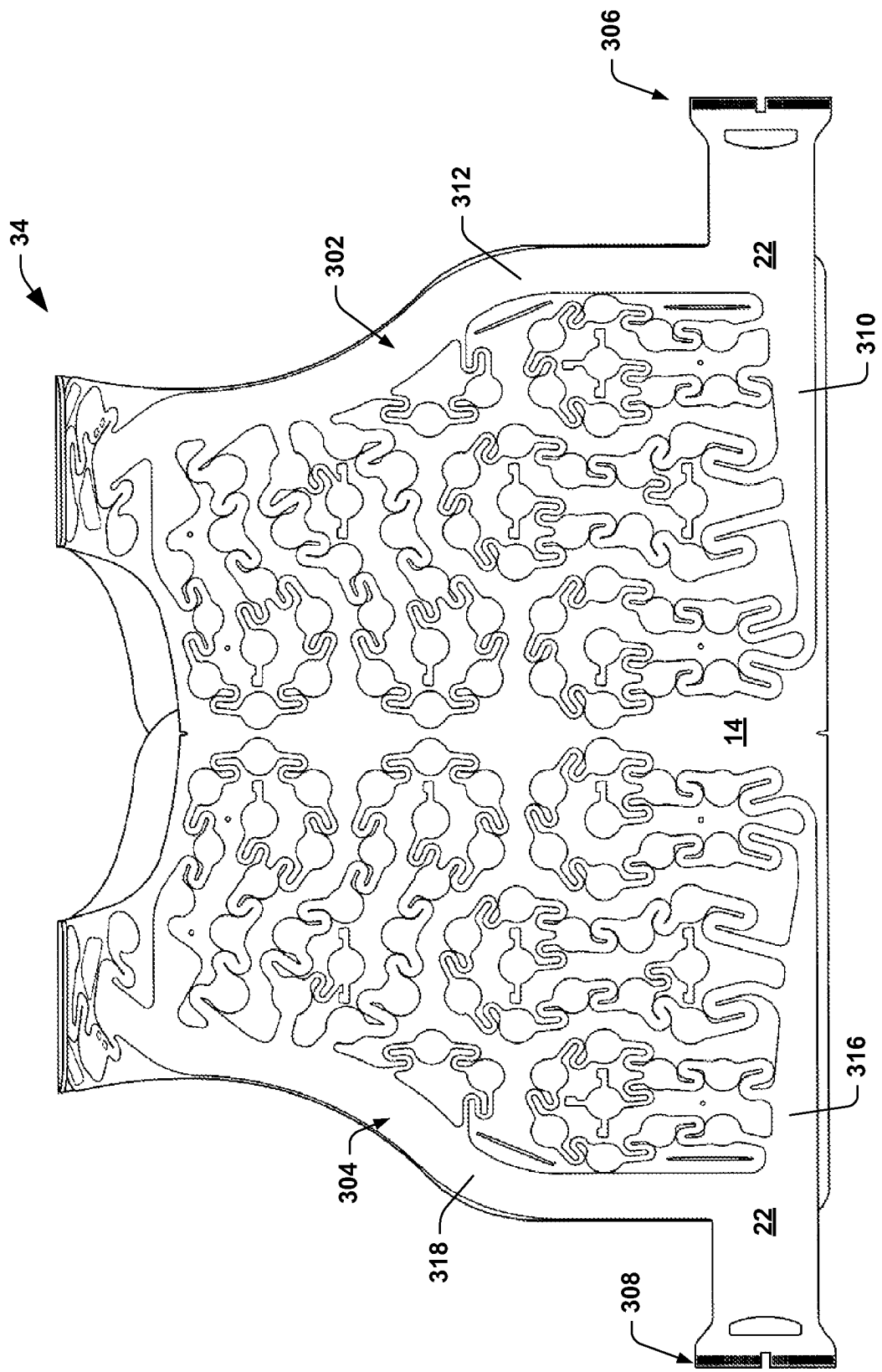
FIG. 16 depicts an example of a rear elevation of part of the sensor apparatus of FIG. 1 demonstrating an arrangement of electrodes.

FIG. 16 depicts an example of the sensor apparatus of FIG. 1 showing the back section 34 as viewed from the non-contact surface thereof. Accordingly similar reference characters as utilized in the example of FIG. 1 refer to similar portions for the section 34 in the example of FIG. 16. Briefly stated, the sensor section 34 includes a flexible substrate layer 12 that is secured to an elastic conformable layer 14.

In the example of FIG. 16 the section 34 includes a pair of separate structures 302 and 304 corresponding to the flexible substrate layer 12. The flexible structures 302 and 304 can be substantially mirror images of each other to provide an arrangement of electrodes and corresponding circuits for different portions of a patient's body surface to which the section 34 is applied. Each of the structures 302 and 304 can be attached to a common single sheet of the conformable layer 14. Each structure 302 and 304 includes a corresponding terminal connector 306 and 308, respectively. Each of the terminal connectors 308 and 308 thus includes terminals or pins corresponding to each of the electrodes that have been disposed on the respective flexible substrate structures 302 and 304.

As a further example, the substrate layer structure 302 includes a laterally extending base strip portion 310 that extends from the terminal connector 306 in one direction and a second base strip 312 that extends substantially transverse to the first base strip 310. Corresponding loops of the flexible structure extend outwardly from each of the base strip 310 and 312 to provide a corresponding distributed arrangement of electrodes at each of the electrode receiving portions. For example, the loops can include tonsil-shaped and hourglass shaped loops as shown in FIG. 16.

The other flexible structure layer 304 can be similarly configured. The structure includes a pair of base strips 316 and 318 that extend from the terminal connector portion 308. The base strip 316 extends laterally and the base strip 318 extends generally transverse to the lateral base strips 316. Corresponding loops of the flexible layer are provided, such as including both tonsil-shaped and hourglass-shaped loop configurations as disclosed herein.

Figure 17:
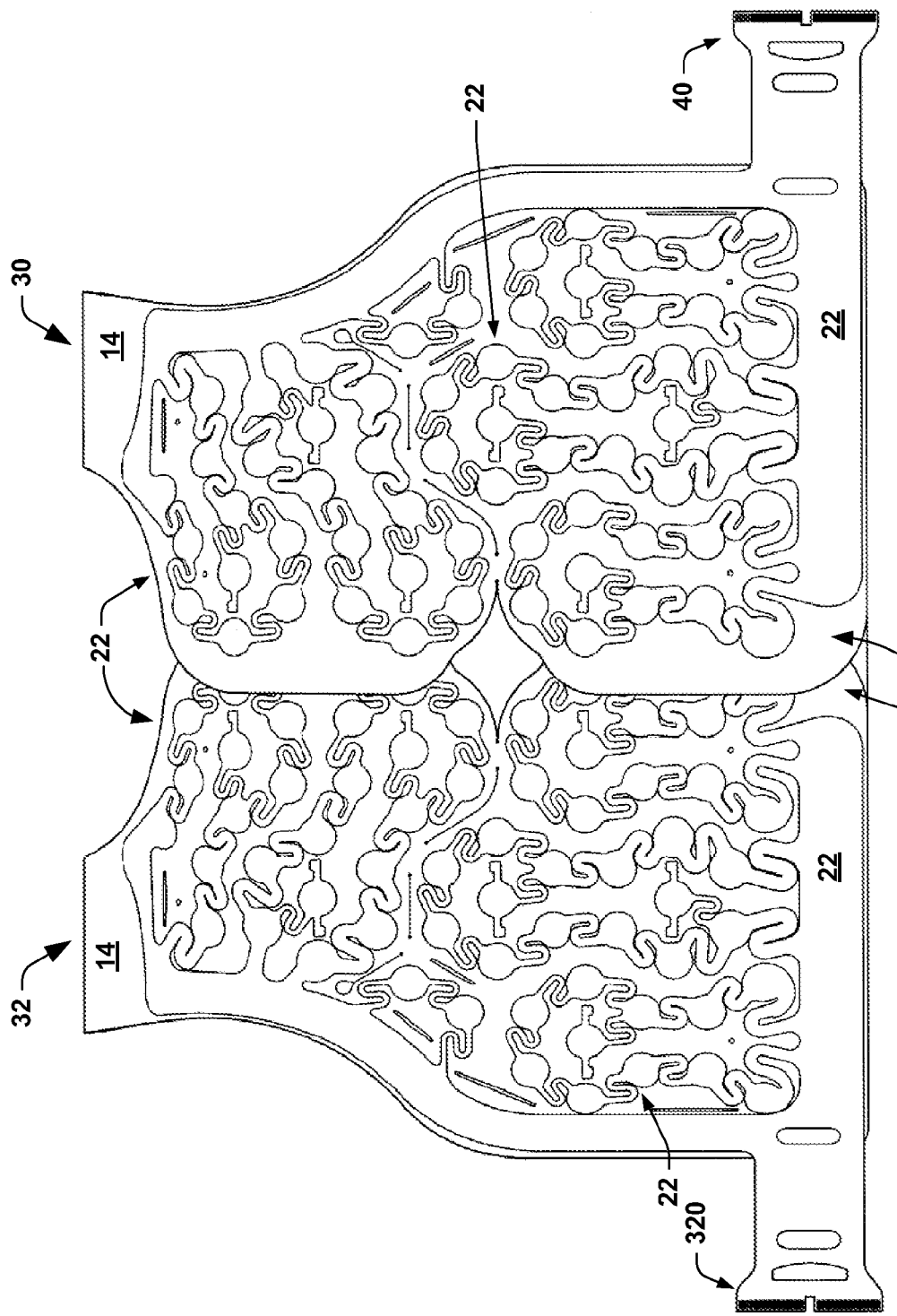
FIG. 17 depicts a front elevation of part of the sensor apparatus of FIG. 1 demonstrating an arrangement of electrodes.

FIG. 17 depicts a front view of the sensor apparatus 10 of FIG. 1 demonstrating a front elevation of the sensor section 30 and 32. The sensor sections 30 and 32 are demonstrated as being separate in contrast to the section 34 of FIG. 16 which has a unitary elastic conformable layer 14. In other examples, the sections can be integrated onto a common single sheet of the conformable layer or they can be separated into a greater number of sheets of the conformable layer. Each such sheet can be employed to provide corresponding sensor apparatus.

As shown in FIG. 17, the section 30 includes a corresponding terminal connector 40 to which the electrical traces for carrying electrical signals from electrodes to associated equipment are connected. Similarly, the section 32 includes a corresponding connector 320 that includes pins or terminals for each of the electrodes disposed on a contact surface of such section. The corresponding connector portions 40 and 320 thus can be configured to extend outwardly away from the patient to facilitate their connection to associated equipment. By employing a pair of sections 30 and 32, an arrangement of electrodes can be provided similar to the section 34 demonstrated in FIG. 16. Thus each of the sections 30 and 32 includes corresponding loop portions 22, such as including the substantially tonsil-shaped and hourglass-shaped loop configurations disclosed herein.

Figure 18:
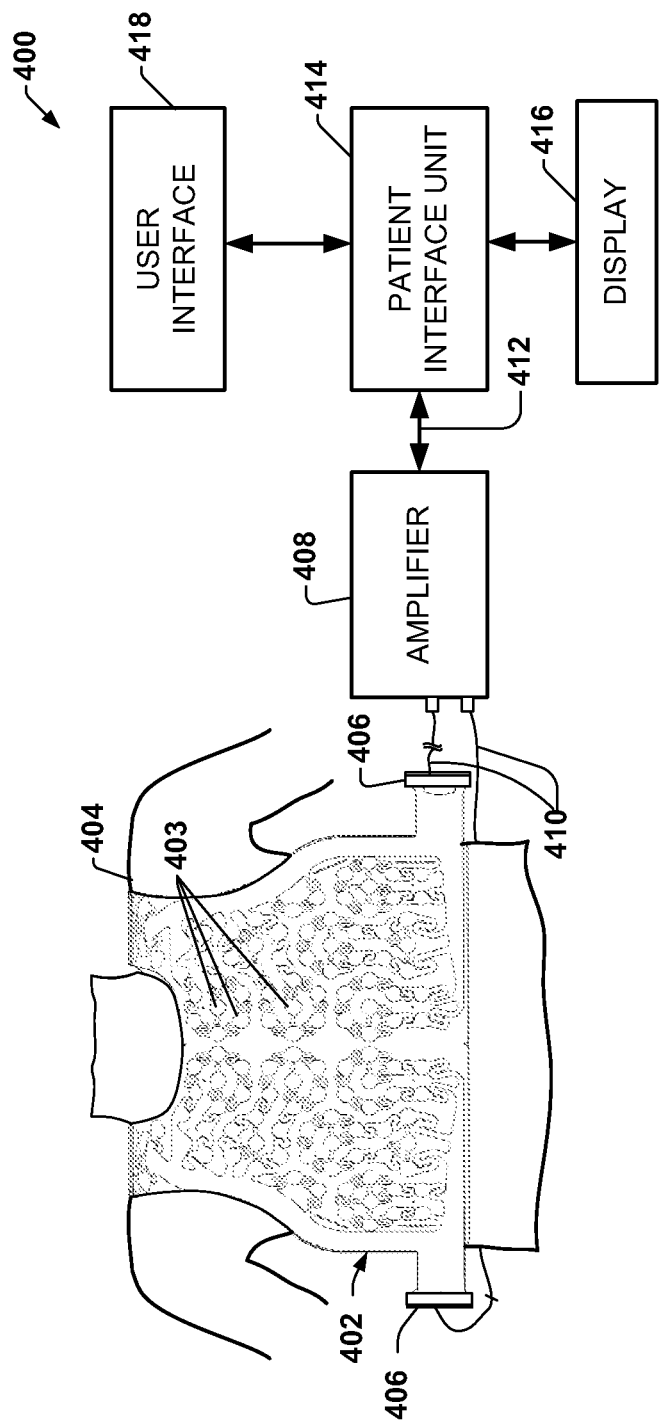
FIG. 18 demonstrates of an example of a sensing system that can be implemented with a sensor apparatus disclosed herein.

FIG. 18 depicts an example of a sensor data acquisition system 400 that can be utilized to acquire data from a sensor apparatus 402 having a plurality of electrical sensors 403 applied to a patient's torso 404, such as corresponding to the electrode structures shown and described herein. The sensor apparatus 402 in the example of FIG. 18 can be in the form of any of the examples disclosed herein (see, e.g., FIGS. 1-17). For instance, to acquire desired data for body surface mapping or electrocardiographic (EC) mapping, the sensing apparatus (e.g., a vest structure formed of corresponding panels constructed according to FIG. 1) 402 can be applied to the patient's torso 404 as to completely cover the patient's torso with a generally evenly distributed arrangement of plurality sensors (e.g., about 250 sensors). To facilitate positioning of the sensor apparatus 10 on the patient, for example, a variety of anatomical markers can be located on the surface.

In the example view shown in FIG. 18, a back sensor section of the vest is shown applied to the patient's torso. Other sensors apparatuses can include sensors covering the front, shoulders and sides of the patient's upper torso above the waist. In other examples, differently configured sections having a fewer or greater number of sensors and/or a different distribution of sensors can be implemented for other purposes.

Connectors from 406 the sensor apparatus 402 can be electrically connected to an amplifier 408 via electrically conductive cables, schematically indicated at 410. In one example, the cables 410 from the sensor assembly flow in a direction toward the left side of the patient such as where the amplifier can be located. Each of the cables 410 can provide a set of input signals to the amplifier 408, and there can be any number of such cables depending on, for example, the configuration of the sensor apparatus 402. The amplifier 406 can receive and aggregate multiple sets of cables 410 from different sensor circuits (e.g., one cable for connecting each circuit to a corresponding input of the amplifier 408). The amplifier 408 can be configured to amplify the signals from each of the sensors and provide a set of amplified electrical signals via an output bus 412 to a patient interface unit 414.

The amplifier 408 may include some signal processing circuitry, such as for filtering signals to remove noise.

A corresponding display 416 can be communicatively coupled with the patient interface unit 414. A user interface (e.g., a graphical user interface) 418 can be associated with the patient interface unit 414, such as for enabling a user to control the data acquisition process and to ensure that appropriate sensor connections have been made. The display 416 may present the GUI to facilitate such controls. The patient interface unit 414 can also be programmed to provide various features associated with the sensors and the data acquisition process. For example, the patient interface unit 414 can be a specially-programmed computer (or other device) that include a processor and memory. The memory can be programmed with machine readable instructions that can be accessed by the processor for performing the functions disclosed herein.

As an example, a user can employ a pointing device (e.g., a mouse or touch screen) or other input device (e.g., a keyboard or gesture control) to interact with the patient interface unit 414. Such interactions can change the graphical and textual information on the display 416. For instance, the user interface 418 can be utilized to change between different sensor views or to enable interaction between multiple views that may be displayed concurrently for different parts of the system 400.

As another example, a user can select one or more sensors 403 via the user interface 418, such as can be presented on the display 416 as part of an interactive graphical representation of a torso. Several different interactive views of the sensor apparatus 402 can be provided, which can be utilized to configure and select the sensors 403. For instance, a user can also employ the user interface 418 select a sensor, and drag and drop it (or shift—select or click a "modify" button and then select) in the other view to update the sensor registration information associated with one or more of the sensors.

Figure 19:
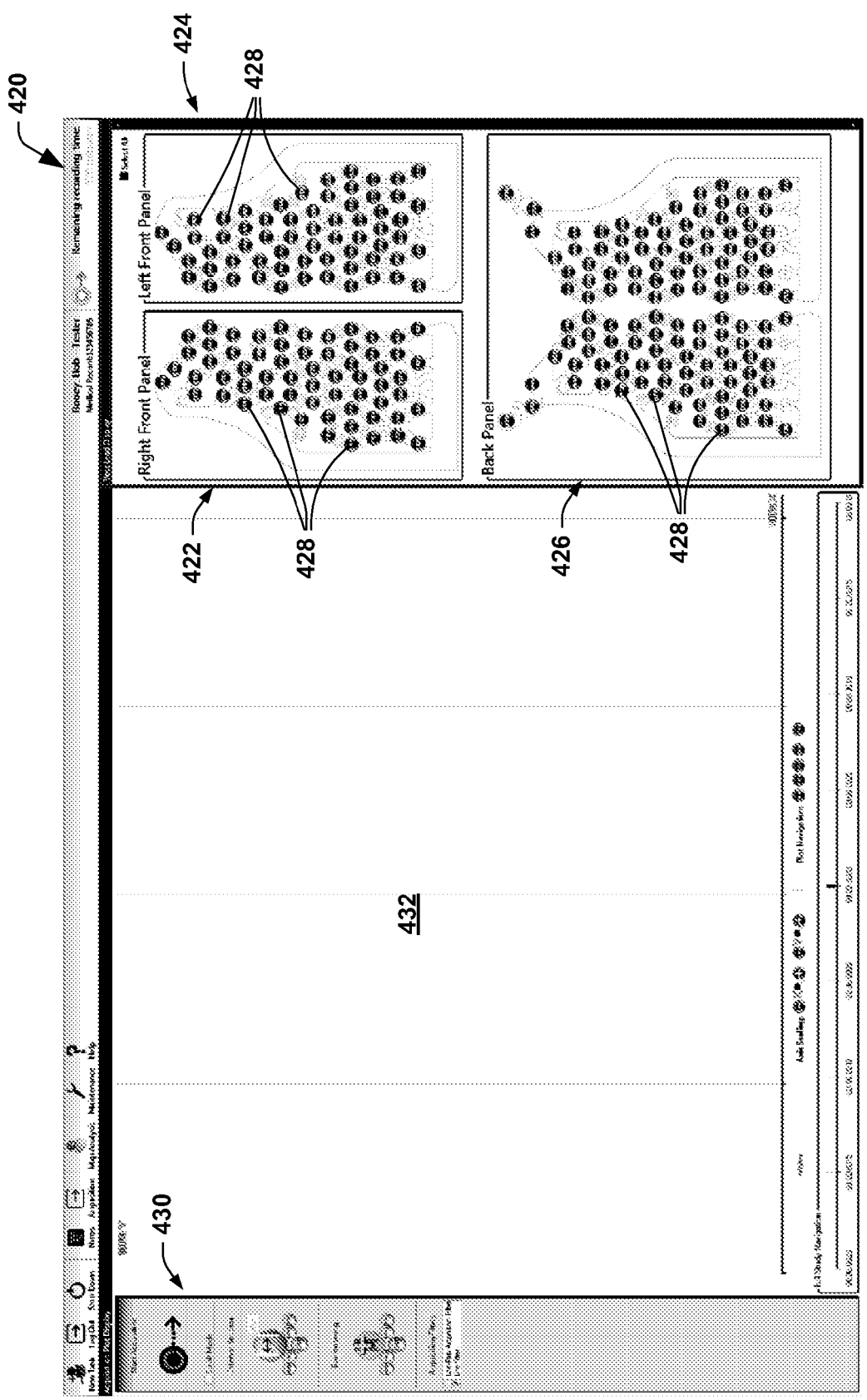
FIG. 19 depicts and example of a graphical user interface that can be implemented in the system of FIG. 18.

An example GUI 420 (e.g., corresponding to the user interface 418 of FIG. 18) is demonstrated in FIG. 19. In discussing the GUI, reference will be to the system 400 of FIG. 18. The GUI 420 can include sensor mapping GUI elements for the set of sensors in each of the panel sections that have been applied to the patient, including the right front panel 422, the left front panel 424 and the back panel 426. Thus the GUI elements 422, 424 and 426 each includes sensor GUI objects for each of the sensors 428 in each panel. The sensor GUI objects 428 can provide information about each sensor 403 such as an indication (e.g., a check mark, or a warning sign) about whether or not information acquired from one or more sensor is consistent with expected information. For example, the patient interface unit 414 can be programmed to analyze known sensor layout and information that the user may have entered, such as for "removed" leads. This can be utilized for validation and registration of the sensors prior to (e.g., during a set-up phase) as well as during the data acquisition process.

As mentioned above, the sensor mapping GUIs 422, 424 and 426 can be programmed to provide a graphical representation of sensors as well as information about their operational status. In the example of FIG. 19, the GUI 420 provides a two-dimensional representation of each of the plurality of sensors 428. In other examples, a three-dimensional representation may be provided. Each of the sensors GUI objects 428 may also include identifiers corresponding to the labels printed on individual sensors 403, such as described herein with respect to the sensor array sections (e.g., FIG. 15), to facilitate locating respective sensors.

Each sensor mapping GUI 422, 424 and 426 can also provide status or connection information about individual sensors and/or cabling to the user performing the data acquisition process, such as can be displayed on sensor GUI objects 428 associated with each of the respective sensors 403. For example, a bad channel (or channels) can be identified by an automated detection process implemented by the patient interface unit 414. The indication of whether a sensor or channel might be functioning outside of expected operating parameters can be visualized by a graphical (e.g., a color code or symbol) and/or text based indication on the corresponding sensor GUI objects 428. Alternatively and additionally, a user can employ an input device to manually mark one or more sensors GUI objects 428 on one or more of the mapping GUIs 422, 424 and 426, such as sensors that might have been removed or repositioned (e.g., as in the case when a defibrillator patch or other pads may be utilized in combination with the sensor array assembly during the data acquisition process).

Additionally or alternatively, sensor layout information can be provided to the patient interface unit 414 based on an integrated circuit that can be incorporated into the sensor apparatus 402. The amount of information may include, for example, information about the types of sensors, the number of sensors, the spatial geometry of the sensors or other information that may be useful to the data acquisition process (e.g., diagnostic information). This information can be provided to the patient interface unit 414 through a separate connection (not shown), which may be wired or wireless, for example.

The patient interface unit 414 further can be programmed to provide real-time (or near real-time) visual representation of electrical activity measured for the patient. This information can be provided in a signal display portion 432 of the GUI 420. As one example, the analysis and processing can be performed as part of a pre-operative procedure. Alternatively or additionally, the analysis and processing can be performed intraoperatively, such as in conjunction with use of an electrophysiology catheter for the patient (e.g., for an EP study, cardiac resynchronization therapy or other procedure).

For example, the user can view electrical data for one or more sensors (e.g., selected via GUI objects 428) that has been acquired for respective sensors on the sensor apparatus 404. The user can manually, via GUI buttons 430, start, stop or otherwise control parameters during the acquisition process. The user can also add markers or annotations to the acquired data via GUI buttons, such as to identify instances of patient movement or other relevant information during the acquisition process.

As another example, the user interface 418 can provide the user with a twelve lead display of the type typically utilized for EC mapping or other types of studies. In this case, the twelve leads corresponding to traditional ECG locations can be automatically selected by the software (e.g., running in a processor of the patient interface unit) according to the spatial position of the sensors in the sensor array applied to the patient. Alternatively or additionally, the user can manually (e.g., via a sensor GUI objects) select the set of sensors that will be used to generate the 12 lead display. As mentioned herein, a set of selected electrodes from the front section can be repositioned to specified locations corresponding to lead locations for the 12 lead ECG. The resulting ECG can be graphically displayed to the user such as in the display portion 432. Other number of channels can also be selected.

What have been described above are examples. It is, of course, not possible to describe every conceivable combination of components or methodologies, but one of ordinary skill in the art will recognize that many further combinations and permutations are possible. Accordingly, the disclosure is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A sensor array apparatus comprising:
   a first substrate layer of a flexible material comprising:
      an elongated base strip; and
      at least one loop of the flexible material, the at least one loop including a first end connected to the elongated base strip and a second end connected to the elongated base strip, the at least one loop further including a first side portion extending outwardly from the first end thereof and a second side portion returning to connect the second side portion and the second end to the elongated base strip;
   a plurality of electrodes distributed along the at least one loop on a contact surface of the first substrate layer;
   electrically conductive paths disposed on the contact surface of the first substrate layer and extending from each of the electrodes to which it is connected and terminating in a corresponding terminal end thereof; and
   a second substrate layer of a stretchable and conformable material, the first substrate layer being affixed to the second substrate layer and configured, such that spaced apart and interconnected portions of the first substrate layer, which include the electrodes, stretch and conform commensurate with movement of the second substrate layer.

2. The sensor array apparatus of claim 1, wherein the first substrate layer further comprises:
   a plurality of electrode receiving portions, each of the electrode receiving portions having a contact surface on which a respective one of the plurality of electrodes is disposed; and
   curved strips that interconnect at least some adjacent pairs of the electrode receiving portions, the curved strips facilitating conformability and stretchability of the interconnected electrode receiving portions in at least two dimensions and enable conformation in more than one plane.

3. The sensor array apparatus of claim 2, wherein at least a substantial number of the curved strips comprises a generally s-shaped length of the flexible material that interconnects a pair of electrode receiving portions, respective electrodes disposed on the contact surface of the pair of electrode receiving portions being electrically connected together by a respective electrically conductive path that follows the s-shaped length of the flexible material.

4. The sensor array apparatus of claim 3, wherein the s-shaped length of the flexible material has a width that is less than a diameter of each pair of electrode receiving portions that the s-shaped length interconnects.

5. The sensor array apparatus of claim 2, wherein the second substrate layer further comprise a frangible portion to facilitate separating and repositioning an anatomically selected portion of the second substrate layer and the first substrate layer affixed thereto, whereby, when attached to a patient, access to a portion of the patient's body beneath the anatomically selected portion is provided.

6. The sensor array apparatus of claim 1, wherein the first side portion of the at least one loop extends outwardly from the first end thereof and curves inwardly back toward the elongated base strip to provide a bulbous loop portion at a distal end of the at least one loop spaced apart from the elongated base strip, and the second side portion returning from the distal end to the elongated base strip to connect the second side portion and the second end to the elongated base strip adjacent the first end.

7. The sensor array apparatus of claim 6, wherein the first side portion and the second side portion curve inwardly toward each other to provide an intermediate tapered portion of the loop, the first side portion and the second side portion further extending outwardly from the base strip to provide the bulbous loop portion that interconnects the intermediate tapered portion by curving outwardly away from each other and then toward each other to provide the distal end of the loop.

8. The sensor array apparatus of claim 7, wherein the at least one loop comprises a plurality of loops, the plurality of loops being configured such that the bulbous loop portion of one loop is located adjacent and follows a contour of the intermediate tapered portion of an adjacent loop.

9. The sensor array apparatus of claim 6, wherein the first substrate layer of the flexible material further comprises a central electrode receiving portion located approximately in a central position of the bulbous loop portion, an electrode being disposed on the contact surface of the central electrode receiving portion.

10. The sensor array apparatus of claim 9, wherein the first substrate layer of the flexible material further comprises a generally s-shaped curved strip that interconnects the central electrode receiving portion with another part of the loop.

11. The sensor array apparatus of claim 6, wherein the loop is substantially symmetrical.

12. The sensor array apparatus of claim 6, wherein the loop comprises a substantially hourglass-shaped loop that includes a pair of bulbous end portions at each of its ends.

13. The sensor array apparatus of claim 6, wherein the base strip comprises a first base strip and a second base strip that extends outwardly from the first base strip substantially transverse to the first base strip,
the at least one loop comprising a plurality of loops, a first set of the plurality of loops extending outwardly from the first base strip and a second set of the plurality of loops extending outwardly from the second base strip.

14. The sensor array apparatus of claim 13, wherein the electrodes are disposed along each of the plurality of loops to provide a substantially even distribution of electrodes along the contact surface thereof.

15. The sensor array apparatus of claim 14, wherein the plurality of loops are configured and dimensioned such that the bulbous loop portion of one loop is located adjacent and follows a contour of an intermediate tapered portion of an adjacent loop.

16. The sensor array apparatus of claim 1, further comprising:
a first sensor array section configured for placement on a right-side front portion of a patient's torso;
a second sensor array section configured for placement on a left-side front portion of the patient's torso;
a third sensor array section configured for placement on a back portion of the patient's torso; and
wherein the first second and third sensor array sections, when placed on the patient's torso, provide a generally evenly distributed arrangement of sensors that circumscribe the patient's torso.

17. The sensor array apparatus of claim 16,
wherein the electrodes and electrically conductive paths of the first sensor array section defines a first electrical circuit attached to a common first sheet of the second substrate layer;
wherein the electrodes and electrically conductive paths of the second sensor array section defines a second electrical circuit attached to a common second sheet of the second substrate layer; and
wherein the electrodes and electrically conductive paths of the third sensor array section defines a third electrical circuit attached to a common third sheet of the second substrate layer.

18. The sensor array apparatus of claim 1, wherein the first substrate layer of the flexible material further comprises a monolithic layer that includes a plurality of loops, a plurality of the electrodes being distributed along respective electrically conductive paths for each of the plurality of loops.

19. The sensor array apparatus of claim 18, wherein at least some of the plurality of loops comprise tonsil-shaped loops.

20. The sensor array apparatus of claim 18, wherein at least some of the plurality of loops comprise hourglass-shaped loops.

21. The sensor array apparatus of claim 1, wherein the electrodes comprise at least one of silver or silver chloride.

22. The sensor array apparatus of claim 1, further comprising an insulating layer disposed over the electrically conductive paths and the contact surface of the first substrate layer such that electrically conductive paths, except for the electrodes, are electrically insulated.

23. A sensing system comprising the sensor array apparatus of claim 1, wherein each of the plurality of electrically conductive paths terminates in at least one respective terminal end of the sensor array apparatus, each electrically conductive path defining a respective channel for each of the plurality of electrodes, the system further comprising:
an amplifier communicatively coupled the at least one terminal end and configured to amplify signals received via each respective channel.

24. A sensor apparatus, comprising:
an electrode carrying layer of a flexible material, the electrode carrying layer comprising a plurality of loop portions of the flexible material, each loop portion having a first end connected to a base strip of the flexible material and a second end spaced apart from the first end connected to the base strip, the first end and extending from the base strip along an arcuate path and terminating via the second end at the base strip;
a plurality of electrodes disposed on a contact surface of the electrode carrying layer and distributed along each of the plurality of loop portions such that the electrodes in each of the plurality of loop portions move commensurate with movement of the electrode carrying layer; and
a plurality of electrically conductive paths electrically extending from a respective electrode and terminating at a terminal end of the electrically conductive path, terminal ends for electrodes of at least one of the plurality of loop portions being located at a common connector.

25. The sensor apparatus of claim 24, further comprising a conformable layer of a stretchable and conformable material, the electrode carrying layer being mounted to the conformable layer.

26. The sensor apparatus of claim 24, wherein at least some of the plurality of loop portions comprise a bulbous loop portion.

27. The sensor apparatus of claim 24, wherein at least some of the plurality of loop portions comprise tonsil-shaped loop portions.

28. The sensor apparatus of claim 24, wherein at least some of the plurality of loop portions comprise hourglass-shaped loop portions.

29. The sensor apparatus of claim 24, wherein the electrode carrying layer comprises a polymer, the sensor apparatus further comprising an insulating layer applied over the electrically conductive paths and the contact surface of the electrode carrying layer such that electrically conductive paths, except for at the electrodes and connectors, are electrically insulated by the insulating layer.

30. The sensor apparatus of claim 24, wherein the base strip comprises a first base strip, the sensor apparatus comprising and a second base strip that extends outwardly from the first base strip substantially transverse to the first base strip, a connector extending from a juncture between the first and second base strips, a first set of the plurality of loop portions extending outwardly from the first base strip and a second set of the plurality of loop portions extending outwardly from the second base strip.

31. The sensor array apparatus of claim 30, wherein the electrodes are disposed along each of the plurality of loop portions to provide a substantially even distribution of electrodes along the contact surface of the electrode carrying layer.

32. The sensor apparatus of claim 25, further comprising:
a first sensor apparatus section configured for placement on a right-side front portion of a patient's torso;
a second sensor apparatus section configured for placement on a left-side front portion of the patient's torso;
a third sensor apparatus section configured for placement on a back portion of the patient's torso.

33. The sensor array apparatus of claim 32,
wherein the electrodes and electrically conductive paths of the first sensor apparatus section defines a first electrical circuit disposed on a first monolithic layer of the electrode carrying layer that is attached to a common first sheet of the conformable layer;
wherein the electrodes and electrically conductive paths of the second sensor apparatus section defines a second electrical circuit disposed on a second monolithic layer of the electrode carrying layer that is attached to a common second sheet of the conformable layer; and
wherein the electrodes and electrically conductive paths of the third sensor apparatus section defines a third electrical circuit disposed on a third monolithic layer of the electrode carrying layer that is attached to a common third sheet of the conformable layer.

\* \* \* \* \*